United States Patent
Kangas et al.

(10) Patent No.: US 9,056,152 B2
(45) Date of Patent: Jun. 16, 2015

(54) MEDICAL DEVICE WITH CRYSTALLINE DRUG COATING

(75) Inventors: Steve Kangas, Woodbury, MN (US); James Feng, Maple Grove, MN (US); Yen-Lane Chen, New Brighton, MN (US); Maggie Zeng, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 139 days.

(21) Appl. No.: 13/242,445

(22) Filed: Sep. 23, 2011

(65) Prior Publication Data

US 2013/0053947 A1 Feb. 28, 2013

Related U.S. Application Data

(60) Provisional application No. 61/527,203, filed on Aug. 25, 2011.

(51) Int. Cl.
*A61L 33/00* (2006.01)
*A61L 27/54* (2006.01)
(Continued)

(52) U.S. Cl.
CPC .............. *A61L 27/54* (2013.01); *A61K 31/337* (2013.01); *C09D 5/16* (2013.01); *A61F 2/02* (2013.01); *A61F 2/00* (2013.01); *A61L 29/16* (2013.01); *A61L 31/16* (2013.01); *A61L 2300/416* (2013.01); *A61L 2300/63* (2013.01)

(58) Field of Classification Search
CPC ............ A61M 25/10; A61F 2/02; A61F 2/00; C09D 5/16

USPC ................. 604/509; 424/423, 448; 429/195.1
See application file for complete search history.

(56) References Cited

U.S. PATENT DOCUMENTS

| 304,121 A | 8/1884 | Munch |
| 4,026,296 A | 5/1977 | Stoy |

(Continued)

FOREIGN PATENT DOCUMENTS

| CA | 2363119 | 8/2000 |
| DE | 19908318 | 8/2000 |

(Continued)

OTHER PUBLICATIONS

Mondesire (Targeting Mammalian Target of Rapamycin Synergistically Enhances Chemotherapy-Induced Cytotoxicity in Breast Cancer Cells, 10 Clin. Cancer Res. 7031 (2004).

(Continued)

*Primary Examiner* — Dah-Wei D Yuan
*Assistant Examiner* — Andrew Bowman
(74) *Attorney, Agent, or Firm* — Vidas, Arrett & Steinkraus

(57) ABSTRACT

A medical device having a polymer-free outer surface layer comprising a crystalline drug selected from the group consisting of everolimus, tacrolimus, sirolimus, zotarolimus, biolimus, and rapamycin. The device may be produced by a method comprising the steps of providing a medical device; applying a solution of the drug to said portion of the outer surface to form a coating of amorphous drug; and vapor annealing the drug with a solvent vapor to form crystalline drug; wherein a seed layer of a crystalline form of said drug having a maximum particle size of about 10 μm or less is applied to at least said portion of the outer surface of the device before or after applying the drug solution, but before vapor annealing the amorphous coating.

16 Claims, 6 Drawing Sheets

(Comparative)

(51) Int. Cl.
*A61L 29/16* (2006.01)
*A61L 31/16* (2006.01)
*A61K 31/337* (2006.01)
*C09D 5/16* (2006.01)
*A61F 2/02* (2006.01)
*A61F 2/00* (2006.01)

(56) References Cited

U.S. PATENT DOCUMENTS

| | | |
|---|---|---|
| 4,186,745 A | 2/1980 | Lewis |
| 4,364,392 A | 12/1982 | Strother |
| 4,481,323 A | 11/1984 | Sterling |
| 4,490,421 A | 12/1984 | Levy |
| 4,515,593 A | 5/1985 | Norton |
| 4,589,873 A | 5/1986 | Schwartz |
| 4,603,152 A | 7/1986 | Laurin |
| 4,610,688 A | 9/1986 | Silvestrini |
| 4,644,936 A | 2/1987 | Schiff |
| 4,693,243 A | 9/1987 | Buras |
| 4,759,758 A | 7/1988 | Gabbay |
| 4,769,013 A | 9/1988 | Lorenz |
| 4,784,647 A | 11/1988 | Gross |
| 4,800,882 A | 1/1989 | Gianturco |
| 4,886,062 A | 12/1989 | Wiktor |
| 4,906,244 A | 3/1990 | Pinchuk et al. |
| 4,931,583 A | 6/1990 | Hull |
| 4,950,239 A | 8/1990 | Gahara |
| 4,950,256 A | 8/1990 | Luther |
| 4,994,033 A | 2/1991 | Shockey |
| 5,026,607 A | 6/1991 | Kiezulas |
| 5,027,996 A | 7/1991 | Fefeu |
| 5,041,100 A | 8/1991 | Rowland |
| 5,049,131 A | 9/1991 | Deuss |
| 5,087,244 A | 2/1992 | Wolinsky |
| 5,091,205 A | 2/1992 | Fan |
| 2,098,381 A | 3/1992 | Schneider |
| 5,092,841 A | 3/1992 | Spears |
| 5,098,381 A | 3/1992 | Schneider |
| 5,102,402 A | 4/1992 | Dror |
| 5,135,516 A | 8/1992 | Sahatjian |
| 5,169,933 A | 12/1992 | Anderson |
| 5,180,366 A | 1/1993 | Woods |
| 5,199,951 A | 4/1993 | Spears |
| 5,213,576 A | 5/1993 | Abiuso |
| 5,213,580 A | 5/1993 | Slepian |
| 5,232,444 A | 8/1993 | Just |
| 5,236,413 A | 8/1993 | Feiring |
| 5,250,069 A | 10/1993 | Nobuyoshi |
| 5,264,260 A | 11/1993 | Saab |
| 5,270,086 A | 12/1993 | Hamlin |
| 5,282,785 A | 2/1994 | Shapland |
| 5,286,254 A | 2/1994 | Shapland |
| 5,295,962 A | 3/1994 | Crocker |
| 5,304,121 A | 4/1994 | Sahatjian |
| 5,318,531 A | 6/1994 | Leone |
| 5,320,634 A | 6/1994 | Vigil |
| 5,324,261 A | 6/1994 | Amundson |
| 5,328,468 A | 7/1994 | Kaneko |
| 5,328,471 A | 7/1994 | Slepian |
| 5,342,628 A | 8/1994 | Picha |
| 5,344,400 A | 9/1994 | Kaneko |
| 5,344,402 A | 9/1994 | Crocker |
| 5,362,831 A | 11/1994 | Mongelli |
| 5,368,566 A | 11/1994 | Crocker |
| 5,370,614 A | 12/1994 | Amundson |
| 5,380,299 A | 1/1995 | Fearnot |
| 5,383,928 A | 1/1995 | Scott |
| 5,385,152 A | 1/1995 | Abele |
| 5,405,472 A | 4/1995 | Leone |
| 5,419,760 A | 5/1995 | Narciso |
| 5,421,826 A | 6/1995 | Crocker |
| 5,425,703 A | 6/1995 | Feiring |
| 5,427,767 A | 6/1995 | Kresse |
| 5,439,446 A | 8/1995 | Barry |
| 5,443,496 A | 8/1995 | Schwartz |
| 5,447,724 A | 9/1995 | Helmus |
| 5,449,382 A | 9/1995 | Dayton |
| 5,464,650 A | 11/1995 | Berg |
| 5,470,307 A | 11/1995 | Lindall |
| 5,489,525 A | 2/1996 | Pastan |
| 5,498,238 A | 3/1996 | Shapland |
| 5,499,971 A | 3/1996 | Shapland |
| 5,500,180 A | 3/1996 | Anderson |
| 5,542,926 A | 8/1996 | Crocker |
| 5,545,208 A | 8/1996 | Wolff |
| 5,549,603 A | 8/1996 | Feiring |
| 5,554,119 A | 9/1996 | Harrison |
| 5,554,182 A | 9/1996 | Dinh |
| 5,556,383 A | 9/1996 | Wang et al. |
| 5,558,642 A | 9/1996 | Schweich, Jr. |
| 5,562,922 A | 10/1996 | Lambert |
| 5,569,184 A | 10/1996 | Crocker |
| 5,569,463 A | 10/1996 | Helmus |
| 5,571,089 A | 11/1996 | Crocker |
| 5,578,075 A | 11/1996 | Dayton |
| 5,588,962 A | 12/1996 | Nicholas |
| 5,599,306 A | 2/1997 | Klein |
| 5,599,307 A | 2/1997 | Bacher |
| 5,609,629 A | 3/1997 | Fearnot |
| 5,611,775 A | 3/1997 | Machold |
| 5,616,149 A | 4/1997 | Barath |
| 5,624,411 A | 4/1997 | Tuch |
| 5,626,862 A | 5/1997 | Brem |
| 5,628,730 A | 5/1997 | Shapland |
| 5,629,008 A | 5/1997 | Lee |
| 5,634,901 A | 6/1997 | Alba |
| 5,637,086 A | 6/1997 | Ferguson |
| 5,651,986 A | 7/1997 | Brem |
| 5,665,772 A | 9/1997 | Cottens |
| 5,669,874 A | 9/1997 | Feiring |
| 5,674,192 A | 10/1997 | Sahatjian |
| 5,674,241 A | 10/1997 | Bley |
| 5,679,400 A | 10/1997 | Tuch |
| 5,685,847 A | 11/1997 | Barry |
| 5,688,516 A | 11/1997 | Raad |
| 5,693,034 A | 12/1997 | Buscemi |
| 5,697,967 A | 12/1997 | Dinh |
| 5,704,908 A | 1/1998 | Hofmann |
| 5,707,385 A | 1/1998 | Williams |
| 5,716,981 A | 2/1998 | Hunter |
| 5,728,066 A | 3/1998 | Daneshvar |
| 5,733,925 A | 3/1998 | Kunz |
| 5,766,158 A | 6/1998 | Opolski |
| 5,769,883 A | 6/1998 | Buscemi |
| 5,797,877 A | 8/1998 | Hamilton |
| 5,800,538 A | 9/1998 | Slepian |
| 5,807,306 A | 9/1998 | Shapland |
| 5,810,763 A | 9/1998 | Feiring |
| 5,833,657 A | 11/1998 | Reinhardt et al. |
| 5,833,658 A | 11/1998 | Levy |
| 5,843,089 A | 12/1998 | Sahatjian |
| 5,854,382 A | 12/1998 | Loomis |
| 5,855,546 A | 1/1999 | Hastings |
| 5,857,998 A | 1/1999 | Barry |
| 5,865,801 A | 2/1999 | Houser |
| 5,868,719 A | 2/1999 | Tsukernik |
| 5,869,127 A | 2/1999 | Zhong |
| 5,876,374 A | 3/1999 | Alba |
| 5,893,840 A | 4/1999 | Hull |
| 5,900,246 A | 5/1999 | Lambert |
| 5,902,266 A | 5/1999 | Leone |
| 5,902,299 A | 5/1999 | Jayaraman |
| 5,928,279 A | 7/1999 | Shannon |
| 5,935,275 A | 8/1999 | Burgard |
| 5,935,506 A | 8/1999 | Schmitz |
| 5,947,977 A | 9/1999 | Slepian |
| 5,954,693 A | 9/1999 | Barry |
| 5,954,706 A | 9/1999 | Sahatjian |
| 5,977,163 A | 11/1999 | Li |
| 5,981,568 A | 11/1999 | Kunz |
| 6,048,356 A | 4/2000 | Ravenscroft |
| 6,048,515 A | 4/2000 | Kresse |
| 6,048,620 A | 4/2000 | Zhong |

(56) References Cited

U.S. PATENT DOCUMENTS

| | | |
|---|---|---|
| 6,093,463 A | 7/2000 | Thakrar |
| 6,099,454 A | 8/2000 | Hastings |
| 6,099,926 A | 8/2000 | Thakrar |
| 6,129,705 A | 10/2000 | Grantz |
| 6,142,973 A | 11/2000 | Carleton |
| 6,146,356 A | 11/2000 | Wang et al. |
| 6,146,358 A | 11/2000 | Rowe |
| 6,183,658 B1 | 2/2001 | Lesniak |
| 6,186,745 B1 | 2/2001 | Johnson |
| 6,195,583 B1 | 2/2001 | Feiring |
| 6,203,551 B1 | 3/2001 | Wu |
| 6,218,016 B1 | 4/2001 | Tedeschi |
| 6,219,577 B1 | 4/2001 | Brown |
| 6,240,407 B1 | 5/2001 | Chang |
| 6,245,103 B1 | 6/2001 | Stinson |
| 6,262,107 B1 | 7/2001 | Li |
| 6,270,522 B1 | 8/2001 | Simhambhatla |
| 6,280,411 B1 | 8/2001 | Lennox |
| 6,283,947 B1 | 9/2001 | Mirzaee |
| 6,287,332 B1 | 9/2001 | Bolz |
| 6,296,619 B1 | 10/2001 | Brisken |
| 6,299,604 B1 | 10/2001 | Ragheb |
| 6,306,166 B1 | 10/2001 | Barry |
| 6,344,028 B1 | 2/2002 | Barry |
| 6,355,029 B1 | 3/2002 | Joye |
| 6,364,856 B1 | 4/2002 | Ding |
| 6,364,893 B1 | 4/2002 | Sahatjian |
| 6,369,039 B1 | 4/2002 | Palasis |
| 6,389,314 B2 | 5/2002 | Feiring |
| 6,391,033 B2 | 5/2002 | Ryan |
| 6,398,708 B1 | 6/2002 | Hastings |
| 6,409,716 B1 | 6/2002 | Sahatjian |
| 6,418,448 B1 | 7/2002 | Sarkar |
| 6,419,692 B1 | 7/2002 | Yang |
| 6,428,534 B1 | 8/2002 | Joye |
| 6,432,102 B2 | 8/2002 | Joye |
| 6,440,990 B1 | 8/2002 | Cottens |
| 6,443,941 B1 | 9/2002 | Slepian |
| 6,451,373 B1 | 9/2002 | Hossainy |
| 6,468,297 B1 | 10/2002 | Williams |
| 6,494,862 B1 | 12/2002 | Ray |
| 6,506,408 B1 | 1/2003 | Palasis |
| 6,511,477 B2 | 1/2003 | Altman |
| 6,514,245 B1 | 2/2003 | Williams |
| 6,517,533 B1 | 2/2003 | Swaminathan |
| 6,524,274 B1 | 2/2003 | Rosenthal |
| 6,527,740 B1 | 3/2003 | Jackson |
| 6,537,194 B1 | 3/2003 | Winkler |
| 6,541,039 B1 | 4/2003 | Lesniak |
| 6,544,221 B1 | 4/2003 | Kokish |
| 6,544,223 B1 | 4/2003 | Kokish |
| 6,545,097 B2 | 4/2003 | Pinchuk |
| 6,548,569 B1 | 4/2003 | Williams |
| 6,582,353 B1 | 6/2003 | Hastings |
| 6,585,926 B1 | 7/2003 | Mirzaee |
| 6,592,548 B2 | 7/2003 | Jayaraman |
| 6,602,246 B1 | 8/2003 | Joye |
| 6,616,650 B1 | 9/2003 | Rowe |
| 6,623,452 B2 | 9/2003 | Chien |
| 6,623,749 B2 | 9/2003 | Williams |
| 6,638,246 B1 | 10/2003 | Naimark |
| 6,645,135 B1 | 11/2003 | Bhat |
| 6,648,879 B2 | 11/2003 | Joye |
| 6,656,156 B2 | 12/2003 | Yang |
| 6,663,880 B1 | 12/2003 | Roorda |
| 6,682,545 B1 | 1/2004 | Kester |
| 6,685,648 B2 | 2/2004 | Flaherty |
| 6,699,272 B2 | 3/2004 | Slepian |
| 6,706,013 B1 | 3/2004 | Bhat |
| 6,730,105 B2 | 5/2004 | Shiber |
| 6,733,474 B2 | 5/2004 | Kusleika |
| 6,780,324 B2 | 8/2004 | Le Garrec |
| 6,783,543 B2 | 8/2004 | Jang |
| 6,786,900 B2 | 9/2004 | Joye |
| 6,786,901 B2 | 9/2004 | Joye |
| 6,790,224 B2 | 9/2004 | Gerberding |
| 6,796,960 B2 | 9/2004 | Cioanta |
| 6,805,898 B1 | 10/2004 | Wu |
| 6,811,550 B2 | 11/2004 | Holland |
| 6,838,493 B2 | 1/2005 | Williams |
| 6,858,644 B2 | 2/2005 | Benigni |
| 6,863,861 B1 | 3/2005 | Zhang |
| 6,867,247 B2 | 3/2005 | Williams |
| 6,890,339 B2 | 5/2005 | Sahatjian |
| 6,890,583 B2 | 5/2005 | Chudzik |
| 6,899,731 B2 | 5/2005 | Li |
| 6,908,462 B2 | 6/2005 | Joye |
| 6,918,927 B2 | 7/2005 | Bates |
| 6,923,996 B2 | 8/2005 | Epstein |
| 6,939,320 B2 | 9/2005 | Lennox |
| 6,942,680 B2 | 9/2005 | Grayzel |
| 6,955,661 B1 | 10/2005 | Herweck |
| 6,960,346 B2 | 11/2005 | Shukla et al. |
| 6,972,015 B2 | 12/2005 | Joye |
| 6,991,647 B2 | 1/2006 | Jadhav |
| 7,005,414 B2 | 2/2006 | Barnikol |
| 7,008,979 B2 | 3/2006 | Schottman |
| 7,018,371 B2 | 3/2006 | Forman |
| 7,037,319 B2 | 5/2006 | Weber |
| 7,048,714 B2 | 5/2006 | Richter |
| 7,056,533 B2 | 6/2006 | Chudzik |
| 7,060,051 B2 | 6/2006 | Palasis |
| 7,060,062 B2 | 6/2006 | Joye |
| 7,066,904 B2 | 6/2006 | Rosenthal |
| 7,070,576 B2 | 7/2006 | Obrien |
| 7,081,112 B2 | 7/2006 | Joye |
| 7,090,655 B2 | 8/2006 | Barry |
| 7,105,175 B2 | 9/2006 | Schwarz |
| 7,108,684 B2 | 9/2006 | Farnan |
| 7,115,299 B2 | 10/2006 | Kokish |
| 7,150,738 B2 | 12/2006 | Ray |
| 7,160,317 B2 | 1/2007 | McHale |
| 7,166,098 B1 | 1/2007 | Steward |
| 7,179,251 B2 | 2/2007 | Palasis |
| 7,232,486 B2 | 6/2007 | Keri |
| 7,241,455 B2 | 7/2007 | Richard |
| 7,247,338 B2 | 7/2007 | Pui |
| 7,279,002 B2 | 10/2007 | Shaw |
| 7,303,572 B2 | 12/2007 | Melsheimer |
| 7,306,625 B1 | 12/2007 | Stratford |
| 7,323,189 B2 | 1/2008 | Pathak |
| 7,335,184 B2 | 2/2008 | Laguna |
| 7,357,940 B2 | 4/2008 | Richard |
| 7,364,585 B2 | 4/2008 | Weber |
| 7,371,257 B2 | 5/2008 | Sahatjian |
| 7,381,418 B2 | 6/2008 | Richard |
| 7,393,685 B1 | 7/2008 | Jordan |
| 7,402,172 B2 | 7/2008 | Chin et al. |
| 7,407,671 B2 | 8/2008 | Mcbride |
| 7,407,684 B2 | 8/2008 | Spencer |
| 7,459,169 B2 | 12/2008 | Nilsson |
| 7,462,165 B2 | 12/2008 | Ding |
| 7,470,252 B2 | 12/2008 | Mickley |
| 7,473,242 B2 | 1/2009 | Donovan |
| 7,491,188 B2 | 2/2009 | Holman |
| 7,494,497 B2 | 2/2009 | Weber |
| 7,527,604 B2 | 5/2009 | Naimark |
| 7,553,292 B2 | 6/2009 | Kilpatrick |
| 7,563,324 B1 | 7/2009 | Chen |
| 7,572,245 B2 | 8/2009 | Herweck |
| 7,588,642 B1 | 9/2009 | Morris |
| 7,604,631 B2 | 10/2009 | Reynolds |
| 7,632,288 B2 | 12/2009 | Wu |
| 7,682,387 B2 | 3/2010 | Shulze |
| 7,718,213 B1 | 5/2010 | Scheer |
| 7,731,685 B2 | 6/2010 | Ragheb |
| 7,744,644 B2 | 6/2010 | Weber |
| 7,750,041 B2 | 7/2010 | Speck |
| 7,753,876 B2 | 7/2010 | Cervantes |
| 7,758,892 B1 | 7/2010 | Chen |
| 7,762,995 B2 | 7/2010 | Eversull |
| 7,767,219 B2 | 8/2010 | Weber |
| 7,771,740 B2 | 8/2010 | Strickler |
| 7,773,447 B2 | 8/2010 | Kajigaya |

(56) References Cited

U.S. PATENT DOCUMENTS

| | | |
|---|---|---|
| 7,794,751 B2 | 9/2010 | Chudzik |
| 7,803,149 B2 | 9/2010 | Bates |
| 7,811,622 B2 | 10/2010 | Bates |
| 8,291,854 B2 | 10/2012 | Behnisch et al. |
| 2001/0020151 A1 | 9/2001 | Reed |
| 2002/0010489 A1 | 1/2002 | Grayzel |
| 2002/0037358 A1 | 3/2002 | Barry |
| 2002/0041898 A1 | 4/2002 | Unger |
| 2002/0042645 A1 | 4/2002 | Shannon |
| 2002/0151844 A1 | 10/2002 | Yang |
| 2002/0183581 A1 | 12/2002 | Yoe |
| 2003/0028210 A1 | 2/2003 | Boyle |
| 2003/0040712 A1 | 2/2003 | Ray |
| 2003/0060877 A1 | 3/2003 | Falotico |
| 2003/0064965 A1 | 4/2003 | Richter |
| 2003/0077253 A1 | 4/2003 | Palasis |
| 2003/0083740 A1 | 5/2003 | Pathak |
| 2003/0114791 A1 | 6/2003 | Rosenthal |
| 2003/0153870 A1 | 8/2003 | Meyer |
| 2003/0158517 A1 | 8/2003 | Kokish |
| 2003/0233068 A1 | 12/2003 | Jayaraman |
| 2003/0236513 A1 | 12/2003 | Schwarz |
| 2003/0236514 A1 | 12/2003 | Schwarz |
| 2004/0023851 A1 | 2/2004 | Barnikol |
| 2004/0033251 A1 | 2/2004 | Sparer |
| 2004/0034336 A1 | 2/2004 | Scott |
| 2004/0039437 A1 | 2/2004 | Sparer |
| 2004/0044308 A1 | 3/2004 | Naimark |
| 2004/0044404 A1 | 3/2004 | Stucke |
| 2004/0047911 A1 | 3/2004 | Lyu |
| 2004/0059290 A1 | 3/2004 | Palasis |
| 2004/0064093 A1 | 4/2004 | Hektner |
| 2004/0073284 A1 | 4/2004 | Bates |
| 2004/0077948 A1 | 4/2004 | Violante |
| 2004/0086569 A1 | 5/2004 | Sparer |
| 2004/0098014 A1 | 5/2004 | Flugelman |
| 2004/0098108 A1 | 5/2004 | Harder |
| 2004/0111144 A1 | 6/2004 | Lawin |
| 2004/0115273 A1 | 6/2004 | Sparer |
| 2004/0117222 A1 | 6/2004 | Rokosz |
| 2004/0127978 A1 | 7/2004 | Sparer |
| 2004/0137066 A1 | 7/2004 | Jayaraman |
| 2004/0142011 A1 | 7/2004 | Nilsson |
| 2004/0143287 A1 | 7/2004 | Konstantino |
| 2004/0175406 A1 | 9/2004 | Schwarz |
| 2004/0180039 A1 | 9/2004 | Toner |
| 2004/0202691 A1 | 10/2004 | Richard |
| 2004/0210191 A1 | 10/2004 | Farnan |
| 2004/0215169 A1 | 10/2004 | Li |
| 2004/0219214 A1 | 11/2004 | Gravett |
| 2004/0224003 A1 | 11/2004 | Schultz |
| 2004/0224080 A1 | 11/2004 | Epstein |
| 2004/0230176 A1 | 11/2004 | Shanahan |
| 2004/0234575 A1 | 11/2004 | Horres |
| 2004/0260239 A1 | 12/2004 | Kusleika |
| 2005/0015046 A1 | 1/2005 | Weber |
| 2005/0025801 A1 | 2/2005 | Richard |
| 2005/0025802 A1 | 2/2005 | Richard |
| 2005/0025803 A1 | 2/2005 | Richard |
| 2005/0025848 A1 | 2/2005 | Huang |
| 2005/0027283 A1 | 2/2005 | Richard |
| 2005/0037048 A1 | 2/2005 | Song |
| 2005/0037050 A1 | 2/2005 | Weber |
| 2005/0043678 A1 | 2/2005 | Freyman |
| 2005/0055077 A1 | 3/2005 | Marco |
| 2005/0060028 A1 | 3/2005 | Horres |
| 2005/0064005 A1 | 3/2005 | Dinh |
| 2005/0064038 A1 | 3/2005 | Dinh |
| 2005/0101522 A1 | 5/2005 | Speck |
| 2005/0106206 A1 | 5/2005 | Herweck |
| 2005/0129727 A1 | 6/2005 | Weber |
| 2005/0129731 A1 | 6/2005 | Horres |
| 2005/0137618 A1 | 6/2005 | Kunis |
| 2005/0154416 A1 | 7/2005 | Herweck |
| 2005/0158359 A1 | 7/2005 | Epstein |
| 2005/0169969 A1 | 8/2005 | Li |
| 2005/0176678 A1 | 8/2005 | Horres |
| 2005/0181015 A1 | 8/2005 | Zhong |
| 2005/0182361 A1 | 8/2005 | Lennox |
| 2005/0209548 A1 | 9/2005 | Dev |
| 2005/0215722 A1 | 9/2005 | Pinchunk |
| 2005/0220853 A1 | 10/2005 | Dao |
| 2005/0222677 A1 | 10/2005 | Bates |
| 2005/0226991 A1 | 10/2005 | Hossainy |
| 2005/0233061 A1 | 10/2005 | Schwarz |
| 2005/0244456 A1 | 11/2005 | Nilsson |
| 2005/0244459 A1 | 11/2005 | Dewitt |
| 2005/0246009 A1 | 11/2005 | Toner |
| 2005/0251106 A1 | 11/2005 | Cervantes |
| 2005/0273049 A1 | 12/2005 | Krulevitch |
| 2005/0273075 A1 | 12/2005 | Krulevitch |
| 2005/0278021 A1 | 12/2005 | Bates |
| 2005/0288629 A1 | 12/2005 | Kunis |
| 2006/0002968 A1 | 1/2006 | Stewart |
| 2006/0002973 A1 | 1/2006 | Barry |
| 2006/0013853 A1 | 1/2006 | Richard |
| 2006/0013854 A1 | 1/2006 | Strickler |
| 2006/0020243 A1 | 1/2006 | Speck |
| 2006/0020331 A1 | 1/2006 | Bates |
| 2006/0025848 A1 | 2/2006 | Weber |
| 2006/0041225 A1 | 2/2006 | Wallace |
| 2006/0057208 A1 | 3/2006 | Holzer |
| 2006/0058815 A1 | 3/2006 | Mickley |
| 2006/0067977 A1 | 3/2006 | Labrecque et al. |
| 2006/0079836 A1 | 4/2006 | Holman |
| 2006/0083768 A1 | 4/2006 | Labrecque |
| 2006/0085058 A1 | 4/2006 | Rosenthal |
| 2006/0088566 A1 | 4/2006 | Parsonage |
| 2006/0088596 A1 | 4/2006 | Labrecque |
| 2006/0112536 A1 | 6/2006 | Herweck |
| 2006/0121081 A1 | 6/2006 | Labrecque |
| 2006/0121088 A1 | 6/2006 | Hunter |
| 2006/0129093 A1 | 6/2006 | Jackson |
| 2006/0134160 A1 | 6/2006 | Troczynski |
| 2006/0134168 A1 | 6/2006 | Chappa |
| 2006/0135548 A1 | 6/2006 | Keri |
| 2006/0147491 A1 | 7/2006 | Dewitt |
| 2006/0165754 A1 | 7/2006 | Ranade |
| 2006/0167407 A1 | 7/2006 | Weber |
| 2006/0171982 A1 | 8/2006 | Timm |
| 2006/0171984 A1 | 8/2006 | Cromack |
| 2006/0171985 A1 | 8/2006 | Richard |
| 2006/0184112 A1 | 8/2006 | Horn |
| 2006/0190022 A1 | 8/2006 | Beyar |
| 2006/0193890 A1 | 8/2006 | Owens |
| 2006/0193891 A1 | 8/2006 | Richard |
| 2006/0195176 A1 | 8/2006 | Bates |
| 2006/0200048 A1 | 9/2006 | Furst |
| 2006/0200556 A1 | 9/2006 | Brave |
| 2006/0204537 A1 | 9/2006 | Ratner |
| 2006/0212106 A1 | 9/2006 | Weber |
| 2006/0224115 A1 | 10/2006 | Willard |
| 2006/0228452 A1 | 10/2006 | Cromack |
| 2006/0240070 A1 | 10/2006 | Cromack |
| 2006/0280858 A1 | 12/2006 | Kokish |
| 2006/0286071 A1 | 12/2006 | Epstein |
| 2006/0286141 A1 | 12/2006 | Campbell |
| 2007/0003599 A1 | 1/2007 | Schwarz |
| 2007/0020307 A1 | 1/2007 | Zhong et al. |
| 2007/0027523 A1 | 2/2007 | Toner et al. |
| 2007/0067882 A1 | 3/2007 | Atanasoska et al. |
| 2007/0078413 A1 | 4/2007 | Stenzel |
| 2007/0083149 A1 | 4/2007 | Steward et al. |
| 2007/0088246 A1 | 4/2007 | Steward et al. |
| 2007/0088255 A1 | 4/2007 | Toner et al. |
| 2007/0093745 A1 | 4/2007 | Steward et al. |
| 2007/0104766 A1 | 5/2007 | Wang et al. |
| 2007/0106250 A1 | 5/2007 | Seward et al. |
| 2007/0106363 A1 | 5/2007 | Weber |
| 2007/0112330 A1 | 5/2007 | Palasis |
| 2007/0129474 A1 | 6/2007 | Salamone et al. |
| 2007/0129792 A1 | 6/2007 | Picart et al. |
| 2007/0150465 A1 | 6/2007 | Brave et al. |
| 2007/0150466 A1 | 6/2007 | Brave et al. |

(56) References Cited

U.S. PATENT DOCUMENTS

| | | |
|---|---|---|
| 2007/0150470 A1 | 6/2007 | Brave et al. |
| 2007/0150515 A1 | 6/2007 | Brave et al. |
| 2007/0150646 A1 | 6/2007 | Yoon et al. |
| 2007/0154554 A1 | 7/2007 | Burgermeister et al. |
| 2007/0178136 A1 | 8/2007 | Arney |
| 2007/0185561 A1 | 8/2007 | Schmitz et al. |
| 2007/0212386 A1 | 9/2007 | Patravale et al. |
| 2007/0212387 A1 | 9/2007 | Patravale et al. |
| 2007/0212393 A1 | 9/2007 | Patravale et al. |
| 2007/0212394 A1 | 9/2007 | Reyes et al. |
| 2007/0224234 A1 | 9/2007 | Steckel et al. |
| 2007/0225800 A1 | 9/2007 | Sahatjian et al. |
| 2007/0232996 A1 | 10/2007 | Andersen |
| 2007/0244548 A1 | 10/2007 | Myers |
| 2007/0244549 A1 | 10/2007 | Pathak |
| 2007/0254010 A1 | 11/2007 | Richard |
| 2007/0255206 A1 | 11/2007 | Reneker |
| 2007/0292478 A1 | 12/2007 | Youri |
| 2008/0020013 A1* | 1/2008 | Reyes et al. .......... 424/423 |
| 2008/0021385 A1 | 1/2008 | Barry |
| 2008/0027421 A1 | 1/2008 | Vancelette |
| 2008/0031173 A1 | 2/2008 | Zhang |
| 2008/0040314 A1 | 2/2008 | Brave |
| 2008/0050415 A1 | 2/2008 | Atanasoska |
| 2008/0051541 A1 | 2/2008 | Strickler |
| 2008/0057102 A1 | 3/2008 | Roorda |
| 2008/0071350 A1 | 3/2008 | Stinson |
| 2008/0071358 A1 | 3/2008 | Weber |
| 2008/0091008 A1 | 4/2008 | Viswanath |
| 2008/0095847 A1 | 4/2008 | Glauser |
| 2008/0102033 A1 | 5/2008 | Speck |
| 2008/0102034 A1 | 5/2008 | Speck |
| 2008/0104004 A1 | 5/2008 | Brave |
| 2008/0113081 A1 | 5/2008 | Hossainy |
| 2008/0114331 A1 | 5/2008 | Holman |
| 2008/0118544 A1 | 5/2008 | Wang |
| 2008/0132992 A1 | 6/2008 | Bates |
| 2008/0140002 A1 | 6/2008 | Ramzipoor |
| 2008/0145396 A1 | 6/2008 | Bates |
| 2008/0145398 A1 | 6/2008 | Bates |
| 2008/0157444 A1 | 7/2008 | Melsheimer |
| 2008/0171129 A1 | 7/2008 | Ranade |
| 2008/0175887 A1 | 7/2008 | Wang |
| 2008/0195042 A1 | 8/2008 | Weber |
| 2008/0195079 A1 | 8/2008 | Moore |
| 2008/0199506 A1 | 8/2008 | Horres |
| 2008/0206304 A1 | 8/2008 | Lindquist |
| 2008/0208182 A1 | 8/2008 | Lafontaine |
| 2008/0220041 A1 | 9/2008 | Brito |
| 2008/0249464 A1 | 10/2008 | Spencer |
| 2008/0255508 A1 | 10/2008 | Wang |
| 2008/0255509 A1 | 10/2008 | Wang |
| 2008/0255510 A1 | 10/2008 | Wang |
| 2008/0274159 A1 | 11/2008 | Schultz |
| 2008/0276935 A1 | 11/2008 | Wang |
| 2008/0287984 A1 | 11/2008 | Weber |
| 2008/0311173 A1 | 12/2008 | Schwarz |
| 2009/0005849 A1 | 1/2009 | Hossainy |
| 2009/0018501 A1 | 1/2009 | Yribarren |
| 2009/0024200 A1 | 1/2009 | Wilcox |
| 2009/0047414 A1 | 2/2009 | Corbeil |
| 2009/0048667 A1 | 2/2009 | Mochizuki et al. |
| 2009/0054837 A1 | 2/2009 | Von Hoist |
| 2009/0069883 A1 | 3/2009 | Ding |
| 2009/0076448 A1 | 3/2009 | Consigny |
| 2009/0088735 A1 | 4/2009 | Abboud |
| 2009/0098176 A1 | 4/2009 | Helmus |
| 2009/0105686 A1* | 4/2009 | Snow et al. .......... 604/509 |
| 2009/0105687 A1 | 4/2009 | Deckman |
| 2009/0111960 A1 | 4/2009 | Parsonage |
| 2009/0112239 A1 | 4/2009 | To |
| 2009/0120361 A1 | 5/2009 | Schiele |
| 2009/0136560 A1 | 5/2009 | Bates |
| 2009/0187144 A1 | 7/2009 | Jayaraman |
| 2009/0192537 A1 | 7/2009 | Obrien |
| 2009/0204082 A1 | 8/2009 | Wesselmann |
| 2009/0226502 A1 | 9/2009 | Chen |
| 2009/0227948 A1 | 9/2009 | Chen |
| 2009/0227949 A1 | 9/2009 | Knapp |
| 2009/0227980 A1 | 9/2009 | Kangas |
| 2009/0246252 A1 | 10/2009 | Arps |
| 2009/0254063 A1 | 10/2009 | Oepen |
| 2009/0258049 A1 | 10/2009 | Klein |
| 2009/0276036 A1 | 11/2009 | Nagura et al. |
| 2009/0299355 A1 | 12/2009 | Bencini |
| 2009/0299356 A1 | 12/2009 | Watson |
| 2009/0318848 A1 | 12/2009 | Shippy, III |
| 2010/0010470 A1 | 1/2010 | Bates |
| 2010/0015200 A1 | 1/2010 | Mcclain |
| 2010/0023108 A1 | 1/2010 | Toner |
| 2010/0030183 A1 | 2/2010 | Toner |
| 2010/0036585 A1 | 2/2010 | Scharfenberg |
| 2010/0049294 A1 | 2/2010 | Zukowski |
| 2010/0049296 A1 | 2/2010 | Sarasam |
| 2010/0049309 A1 | 2/2010 | Bates |
| 2010/0055294 A1 | 3/2010 | Wang |
| 2010/0056985 A1 | 3/2010 | Weber |
| 2010/0063585 A1 | 3/2010 | Hoffmann |
| 2010/0069838 A1 | 3/2010 | Weber |
| 2010/0074934 A1 | 3/2010 | Hunter |
| 2010/0076542 A1 | 3/2010 | Orlowski |
| 2010/0087783 A1 | 4/2010 | Weber |
| 2010/0092540 A1 | 4/2010 | Pinchuk |
| 2010/0096781 A1 | 4/2010 | Huang |
| 2010/0125239 A1 | 5/2010 | Perry |
| 2010/0131043 A1 | 5/2010 | Casas |
| 2010/0145266 A1 | 6/2010 | Orlowski |
| 2010/0179475 A1 | 7/2010 | Hoffmann |
| 2010/0198190 A1 | 8/2010 | Michal |
| 2010/0209471 A1 | 8/2010 | Weber |
| 2010/0209473 A1 | 8/2010 | Dhont |
| 2010/0228333 A1 | 9/2010 | Drasler |
| 2010/0233228 A1 | 9/2010 | Speck |
| 2010/0233236 A1 | 9/2010 | Zhao |
| 2010/0239635 A1 | 9/2010 | McClain |
| 2010/0249702 A1 | 9/2010 | Magana |
| 2010/0256748 A1 | 10/2010 | Taylor |
| 2010/0261662 A1 | 10/2010 | Schreck |
| 2010/0268191 A1 | 10/2010 | Trudel |
| 2010/0272773 A1 | 10/2010 | Kangas |
| 2010/0272778 A1 | 10/2010 | McClain |
| 2010/0285085 A1 | 11/2010 | Stankus |
| 2010/0292641 A1 | 11/2010 | Wijay |
| 2010/0298769 A1 | 11/2010 | Schewe |
| 2010/0312182 A1 | 12/2010 | Adden |
| 2010/0318020 A1 | 12/2010 | Atanasoska |
| 2010/0324645 A1 | 12/2010 | Stankus |
| 2010/0324648 A1 | 12/2010 | Scheller |
| 2010/0331816 A1 | 12/2010 | Dadino |
| 2010/0331947 A1 | 12/2010 | Shalev |
| 2011/0008260 A1 | 1/2011 | Flanagan |
| 2011/0015664 A1 | 1/2011 | Kangas |
| 2011/0020151 A1 | 1/2011 | Tiefenthaler |
| 2011/0054396 A1 | 3/2011 | Kangas |
| 2011/0054443 A1 | 3/2011 | Weber |
| 2011/0087191 A1 | 4/2011 | Scheuermann |
| 2011/0104452 A1* | 5/2011 | Grozea et al. .......... 428/195.1 |
| 2011/0152765 A1 | 6/2011 | Weber |
| 2011/0160645 A1 | 6/2011 | Sutermeister |
| 2011/0160659 A1 | 6/2011 | Clarke |
| 2011/0160698 A1 | 6/2011 | Hoffmann |
| 2011/0178503 A1 | 7/2011 | Kangas |
| 2011/0190864 A1 | 8/2011 | McClain et al. |
| 2011/0196340 A1 | 8/2011 | Barry |
| 2011/0251590 A1 | 10/2011 | Weber |
| 2011/0270152 A1 | 11/2011 | Atanasoska |
| 2011/0275980 A1 | 11/2011 | Weber |
| 2011/0301565 A1 | 12/2011 | Weber |
| 2012/0009596 A1 | 1/2012 | Hsieh |
| 2012/0059316 A1 | 3/2012 | Owens |
| 2012/0078227 A1 | 3/2012 | Kangas |
| 2012/0095396 A1 | 4/2012 | Radhakrishnan |

(56) References Cited

U.S. PATENT DOCUMENTS

| | | |
|---|---|---|
| 2012/0100279 A1 | 4/2012 | Neumann |
| 2012/0231037 A1 | 9/2012 | Levi et al. |
| 2013/0035483 A1 | 2/2013 | Zeng et al. |
| 2013/0053947 A1 | 2/2013 | Kangas et al. |

FOREIGN PATENT DOCUMENTS

| | | |
|---|---|---|
| DE | 102004020856 | 4/2005 |
| EP | 0383429 | 1/1990 |
| EP | 0372088 | 6/1990 |
| EP | 0379156 | 7/1990 |
| EP | 0399712 | 11/1990 |
| EP | 0470246 | 2/1991 |
| EP | 0551182 | 7/1993 |
| EP | 0568310 | 11/1993 |
| EP | 0734721 | 3/1996 |
| EP | 0747069 | 4/1996 |
| EP | 0519063 | 5/1996 |
| EP | 0717041 | 6/1996 |
| EP | 0770401 | 5/1997 |
| EP | 0633796 | 11/1997 |
| EP | 0937469 | 8/1999 |
| EP | 0950386 | 10/1999 |
| EP | 0623354 | 10/2002 |
| EP | 1189553 | 3/2004 |
| EP | 1407726 | 4/2004 |
| EP | 1521603 | 4/2005 |
| EP | 1667760 | 6/2006 |
| EP | 1372737 | 12/2006 |
| EP | 1810665 | 7/2007 |
| EP | 1666071 | 8/2007 |
| EP | 1666070 | 9/2007 |
| EP | 1857127 | 11/2007 |
| EP | 1539266 | 4/2008 |
| EP | 1981559 | 10/2008 |
| EP | 1996246 | 12/2008 |
| EP | 2043704 | 4/2009 |
| EP | 2108390 | 10/2009 |
| EP | 2125058 | 12/2009 |
| EP | 2125060 | 12/2009 |
| EP | 1594459 | 2/2010 |
| EP | 1669092 | 3/2010 |
| EP | 2172242 | 4/2010 |
| EP | 1534356 | 7/2010 |
| EP | 1786487 | 11/2010 |
| EP | 2251050 | 11/2010 |
| EP | 2241341 | 1/2011 |
| GB | 2112646 | 7/1983 |
| GB | 2127839 | 9/1983 |
| JP | 663145 A | 3/1994 |
| JP | 2002240847 | 8/2002 |
| JP | 2003/524465 | 8/2003 |
| JP | 2004/535856 | 12/2004 |
| JP | 2005/507754 | 3/2005 |
| JP | 2006/51369 | 2/2006 |
| RU | 200513564 | 4/2004 |
| WO | 8912478 | 12/1989 |
| WO | 9108790 | 6/1991 |
| WO | 9211896 | 7/1992 |
| WO | 9215286 | 9/1992 |
| WO | 9306792 | 4/1993 |
| WO | 9421308 | 9/1994 |
| WO | 9423787 | 10/1994 |
| WO | 9503036 | 2/1995 |
| WO | 9503083 | 2/1995 |
| WO | 9508305 | 3/1995 |
| WO | 9521636 | 8/1995 |
| WO | 9625176 | 8/1996 |
| WO | 9632907 | 10/1996 |
| WO | 9639949 | 12/1996 |
| WO | 9710011 | 3/1997 |
| WO | 9725085 | 7/1997 |
| WO | 9733552 | 9/1997 |
| WO | 9741916 | 11/1997 |
| WO | 9831415 | 7/1998 |
| WO | 9901458 | 1/1999 |
| WO | 9908729 | 2/1999 |
| WO | 9916500 | 4/1999 |
| WO | 9925336 | 5/1999 |
| WO | 9929353 | 6/1999 |
| WO | 0032238 | 6/2000 |
| WO | 0032267 | 6/2000 |
| WO | 0045744 | 8/2000 |
| WO | 00/62830 | 10/2000 |
| WO | 0149358 | 7/2001 |
| WO | 0160441 | 8/2001 |
| WO | 0238065 | 5/2002 |
| WO | 0243796 | 6/2002 |
| WO | 02/087651 | 7/2002 |
| WO | 02076509 | 10/2002 |
| WO | 03022265 | 3/2003 |
| WO | 03026718 | 4/2003 |
| WO | 03/039612 | 5/2003 |
| WO | 03059430 | 7/2003 |
| WO | 03094991 | 11/2003 |
| WO | 2004028582 | 4/2004 |
| WO | 2004028610 | 4/2004 |
| WO | 2004050140 | 6/2004 |
| WO | 2004060346 | 7/2004 |
| WO | 2004060471 | 7/2004 |
| WO | 2004089958 | 10/2004 |
| WO | 2004091684 | 10/2004 |
| WO | 2005027994 | 3/2005 |
| WO | 2005027996 | 3/2005 |
| WO | 2005032611 | 4/2005 |
| WO | 2005/082434 | 9/2005 |
| WO | 2006036970 | 4/2006 |
| WO | 2006039237 | 4/2006 |
| WO | 2006102359 | 9/2006 |
| WO | 2006108420 | 10/2006 |
| WO | 2006116348 | 11/2006 |
| WO | 2006116989 | 11/2006 |
| WO | 2006130326 | 12/2006 |
| WO | 2007011707 | 1/2007 |
| WO | 2007090382 | 8/2007 |
| WO | 2007090385 | 8/2007 |
| WO | 2007109114 | 9/2007 |
| WO | 2008003298 | 1/2008 |
| WO | 2008014222 | 1/2008 |
| WO | 2008045228 | 4/2008 |
| WO | 2008086794 | 7/2008 |
| WO | 2008089730 | 7/2008 |
| WO | 2008101486 | 8/2008 |
| WO | 2008109114 | 9/2008 |
| WO | 2008125890 | 10/2008 |
| WO | 2008137237 | 11/2008 |
| WO | 2009002855 | 12/2008 |
| WO | 2009014692 | 1/2009 |
| WO | 2009018816 | 2/2009 |
| WO | 2009026914 | 3/2009 |
| WO | 2009036118 | 3/2009 |
| WO | 2009036135 | 3/2009 |
| WO | 2009066330 | 5/2009 |
| WO | 2009096822 | 8/2009 |
| WO | 2009100394 | 8/2009 |
| WO | 2009120361 | 10/2009 |
| WO | 2009121565 | 10/2009 |
| WO | 2009135125 | 11/2009 |
| WO | 2010009335 | 1/2010 |
| WO | 2010021757 | 2/2010 |
| WO | 2010026578 | 3/2010 |
| WO | 2010079218 | 7/2010 |
| WO | 2010080575 | 7/2010 |
| WO | 2010086863 | 8/2010 |
| WO | 2010096476 | 8/2010 |
| WO | 2010111232 | 9/2010 |
| WO | 2010120620 | 10/2010 |
| WO | 2010124098 | 10/2010 |
| WO | 2010146096 | 12/2010 |
| WO | 2010147805 | 12/2010 |
| WO | 2011009096 | 1/2011 |

(56) References Cited

FOREIGN PATENT DOCUMENTS

| | | |
|---|---|---|
| WO | 2011028419 | 3/2011 |
| WO | 2011097103 | 8/2011 |

OTHER PUBLICATIONS

Minghetti P et al: "Sculptured drug-eluting stent for the on-site delivery of tacrolimus", European Journal of Pharmaceutics and Biopharmaceutics E Lsevier Science Publishers B.V. Amsterdam.NL v.No. 73 No. 3 Nov. 1, 2009 pp. 331-336.
U.S. Appl. No. 61/271,167, filed Jul. 17, 2009.
U.S. Appl. No. 13/242,433, filed Sep. 23, 2011.
U.S. Appl. No. 61/224,723, filed Jul. 10, 2009.
PCT Search Report and Written Opinion for PCT/US2011/052937, dated Mar. 29, 2012.
Abstract from Liggins, R. T., Hunter, W. L and Burt, H. M. 'Solid-state characterization of paclitaxel.' Journal of Pharmaceutical Sciences, 86:1458-1463, (1997).
Abstracts from the 70th Scientific Sessions, Orange County Convention center, Orlando, Florida, Nov. 9-12, 1997, Supplement to Circulation, vol. 96, No. 8, Supplement I, 1-341,1-288 and 1-608.
Alexis et al., 'In vitro study of release mechanisms of paclitaxel and rapamycin from drug-incorporated biodegradable stent matrices' Journal of Controlled Release 98 (2004) 67-74.
Axel, Dorothea I., et al., Paclitaxel Inhibits Arterial Smooth Muscle Cell Proliferation and Migration In Vitro and In Vivo Using Local Drug Delivery, Jul. 15, 1997, vol. 96 (2), 636-651.
Axel De Labriolle et al., "Paclitaxel-eluting balloon: From bench to bed", Catheterization and Cardiovascular Interventions, vol. 73. No. 5, Apr. 1, 2009, pp. 643-652.
Buvardi, S., et al., 'Merck Index', 1996, Merck and Co., p. 144.
Cardiovascular and Interventional Radiology, Supplement 1, Sep. 28-Oct. 2, 1997, 158-161.
Charles et al.; 'Ceramide-Coated Balloon Catheters Limit Neointimal Hyperplasia After Stretch Injury in Carotid Arteries' Circ. Res. 2000;87;282-288.
Consigny PM, Barry JJ, Vitali NJ.; 'Local Delivery of an Antiproliferative Drug with Use of Hydrogel-coated Angioplasty Balloons1' J Vasc Intery Radiol. Jul.-Aug. 1994;5(4):553-60.
Cortese et al., "Paclitaxel-coated balloon versus drug-eluting stent during PCI of small coronary vessels, a prospective randomised clinical trial. The PICCOLETO Study", Heart 2010; 96:1291-1296.
Finkelstein et al., "Local Drug Delivery via a Coronary Stent with Programmable Release Pharmocokinetics," 2003, Circulation, 107, 777-784.
International Preliminary Report on Patentability of International Application No. PCT/DE2007/001173 dated Aug. 4, 2009.
J. Wohrle et al., 'Comparison of the heparin coated vs the uncoated Jostent no influence on restenosis or clinical outcome' European Heart Journal, 2001, vol. 22, pp. 1808-1816.
Mastropaolo et al.; 'Crystal and molecular structure of paclitaxel (taxol)' Proc. Natl. Acad. Sci. USA vol. 92, pp. 6920-6924, Jul. 1995.
Partial European Search Report in EP 07005256.8, dated Jan. 25, 2008.
PCT/US 08/72660 Search Report, Nov. 6, 2008.
PCT/US 2005/47235 Search Report, Dec. 28, 2005.
Presentation by Dr. Cortese, "Paclitaxel-eluting balloon versus paclitaxel-eluting stent in small coronary vessel disease." The Piccoleto Trial.
U.S. Appl. No. 61/322,451, filed Apr. 9, 2010.
U.S. Appl. No. 61/330,201, filed Apr. 30, 2010.
U.S. Appl. No. 61/332,544, filed Apr. 9, 2010.
U.S. Appl. No. 61/352,117, filed Jun. 7, 2010.
U.S. Appl. No. 61/379,608, filed Sep. 2, 2010.
U.S. Appl. No. 61/385,849, filed Sep. 23, 2010.
U.S. Appl. No. 61/394,104, filed Oct. 18, 2010.
U.S. Appl. No. 61/421,054, filed Dec. 8, 2010.
Scheller et al., "Treatment of Coronary In-Stent Restenosis with a Paclitaxel-Coated Balloon Catheter", The New England Journal of Medicine, 2006; 355:2113-24.
Scollott, S.J., et al., Taxol Inhibits Neointimal Smooth Muscle Cell Accumulation after Angioplasty in the Rat, 1995, Journal of Clinical Investigation, 95, pp. 1869-1876.
Westedt et al., "Paclitaxel releasing films consisting of poly(vinyl alcohol)-graft-poly(lactide-co-glycolide) and their potential as biodegradable stent coatings." 2006, J Control Release 111, 235-46 (abstract).
Written Opinion for PCT/DE2008/000096.
Xu et al., "Lactic-co-glycolic acid polymer with rapamycin coated stent reduces neo-intimal formation in a porcine coronary model", Journal of Clinical Cardiology, 2004, abstract.
Dowding et al., "Preparation and Swelling Properties of Poly(NIPAM) "Minigel" Particles Prepared by Inverse Suspension Polymerization," Journal of Colloid and Interface Science 221, 268-272 (2000).
Panda et al., "Synthesis and swelling characteristics of poly(N-isopropylacrylamide) temperature sensitive hydrogels crosslinked by electron beam irradiation," Radiation Physics and Chemistry 58 (2000) 101-110.
U.S. Appl. No. 61/394,104, filed Oct. 18, 2010; Inventor: Radhakrishnan et al.
Scheller et al., "A further alternative; Balloons can be coated, as well" Newsletter from annual meeting in DGK Apr. 21, 2006.
Alexis, et al., In vitro study of release mechanisms of paclitaxel and rapamycin from drug-incorporated biodegradable stent matrices, Journal of Controlled Release, 2004, 98, 67-74 (Said to be available online Jun. 10, 2004).
Westedt, et al., Paclitaxel releasing films consisting of poly(vinyl alcohol)-graft-poly-(lactide-co-glycolide) and their potential as biodegradable stent coatings, Journal of Controlled Release, 2006, 111, 235-246.

* cited by examiner

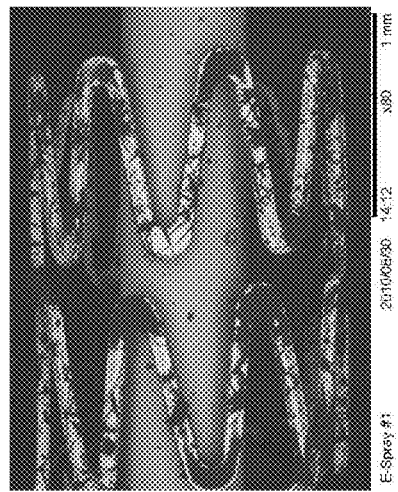
Fig. 8b (Comparative)
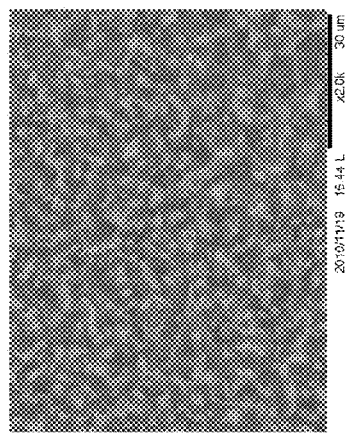
Fig. 7b
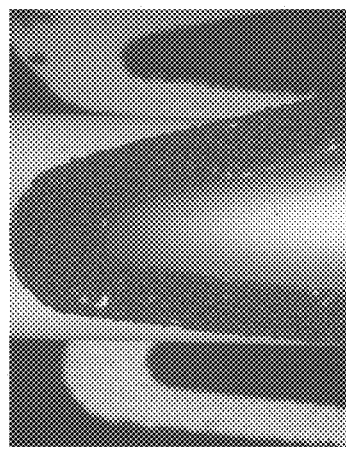
Fig. 7a
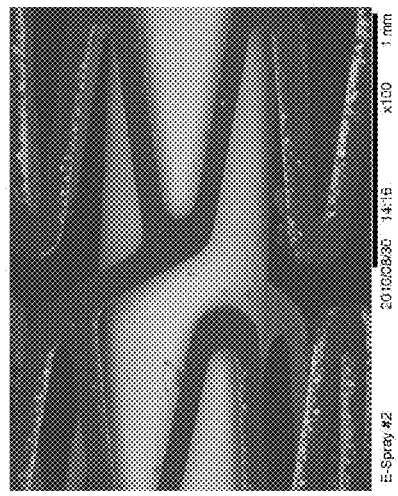
Fig. 8a (Comparative)

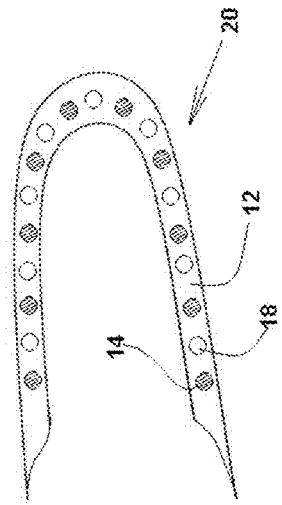
Fig. 11
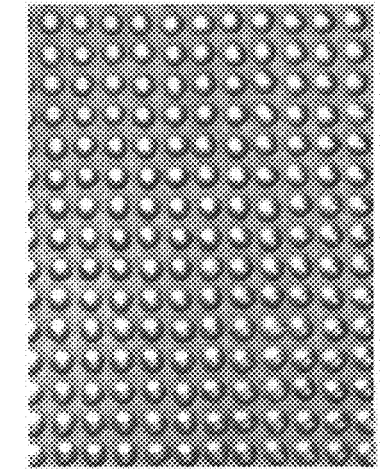
Fig. 10
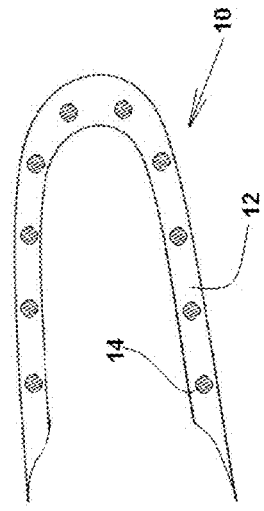
Fig. 13
Fig. 12

“MEDICAL DEVICE WITH CRYSTALLINE DRUG COATING”

MEDICAL DEVICE WITH CRYSTALLINE DRUG COATING

CROSS-REFERENCE TO RELATED APPLICATIONS

This application claims the benefit of U.S. Provisional Application No. 61/527,203, entitled, "Medical Device with Crystalline Drug Coating," by Steve Kangas, James Feng, Maggie Zeng, and Yen-Lane Chen, and filed on Aug. 25, 2011, the entire contents of which being incorporated herein by reference.

BACKGROUND OF THE INVENTION

Medical devices such as catheters, stents or balloons coated with drugs such as paclitaxel and sirolimus, tacrolimus or everolimus, are known. Frequently the drug is compounded with, or absorbed into, a polymer, or is absorbed into a porous material or is coated under a polymer. These techniques can provide for extended release of the drug, but they introduce complicating structural and biocompatibility issues.

Attempts to provide drug coatings that do not include polymers and that provide for extended release of the drug have presented skilled medical device designers with special difficulty.

The problem of providing a polymer-free drug coating specifically on stents is complicated in that a drug coating on the stent should survive expansion of the stent and remain in place until absorbed into tissue or dissolved into the bloodstream. Similar problems exist with other implanted medical devices that are left in the body for extended periods such as artificial heart valves, indwelling catheters, vascular grafts, vena cava filters, stent grafts and the like.

It is desirable however to have an drug coating comprising crystalline drug and at the same time utilizes no polymer. This is a problem because techniques for depositing drug directly on a substrate in crystalline form without a polymer produce very poor adhesion, and other techniques for depositing amorphous drug and then converting it to crystalline form, for instance as described in US 2010/0272773 and US 2011/0015664, commonly owned, and the latter proposes to nucleate the surface, however, the nucleating agent is taught as desirably one that is not soluble in the solvent used to apply the drug, which precludes using the drug itself as a nucleating agent. Water soluble substances are indicated to be preferable.

SUMMARY OF THE INVENTION

The invention in some aspects pertains to a medical device having a polymer-free outer surface layer on at least a portion thereof, said layer comprising a crystalline drug selected from the group consisting of everolimus, tacrolimus, sirolimus, zotarolimus, biolimus, and rapamycin.

In other aspects the invention pertains to a method of forming a coating comprising a drug onto at least a portion of an outer surface of a medical device comprising the steps of
  providing a medical device;
  applying a solution of the drug to said portion of the outer surface to form a coating of amorphous drug; and
  vapor annealing the drug with a solvent vapor to form crystalline drug;
  wherein a seed layer of a crystalline form of said drug having a maximum particle size of about 10 μm or less is applied to at least said portion of the outer surface of the device before or after applying the drug solution, but before vapor annealing the amorphous coating. The drug may be everolimus, tacrolimus, sirolimus, zotarolimus, biolimus, and rapamycin, or other macrolide immunosuppressive drug.

Particularly preferred aspects pertain to such devices and methods where the drug is everolimus and/or where the device is a stent.

Further aspects pertain to such devices or coatings where the drug coating is provided on the stent or the vapor annealing process is controlled to produce a predetermined mixture of crystalline and amorphous drug on the device. Still further aspects of the invention pertain to such medical devices wherein the crystalline form of the drug is formed by individual crystals having with an average length of less than 50 μm, an average width of less than 10 μm and an average thickness of less than 1.5 μm.

These and other aspects and embodiments of the invention are described in the Detailed Description, Claims and Figures which follow.

BRIEF DESCRIPTION OF THE FIGURES

FIGS. 7a and 7b show representative SEM of a vapor annealed seed stent (using the dry everolimus coating process), at two different magnifications. A very small, uniform crystalline structure is formed during vapor annealing.

FIGS. 8a and 8b show a stent coated with amorphous everolimus (FIG. 8a), and after vapor annealing without seeding (FIG. 8b) for comparative purposes.

FIG. 10 shows SEM images of a coated balloon as described in Example 3.

FIG. 11 shows an example of a coating discrete dots of a drug on a substrate.

FIG. 12 depicts a portion of a stent having dots of crystalline drug thereon.

FIG. 13 depicts a portion of a stent having dots of crystalline drug and dots of amorphous drug thereon.

DETAILED DESCRIPTION OF PREFERRED EMBODIMENTS

Earlier investigations of paclitaxel coated balloons by the applicant have shown that it is desirable to control the morphology of the drug on the balloon, that crystalline form drugs can facilitate longer tissue residence time, and that the formation of crystalline paclitaxel dihydrate can be controlled by use of vapor annealing of the balloon. Copending US applications, Ser. No. 12/765,522 filed Apr. 24, 2010, published as US 2010/0272773 A1, claiming priority of provisional application 61/172,629; and Ser. No. 12/815,138, filed Jun. 14, 2010, published as US 2011/0015664 A1 and claiming priority of provisional application 61/271,167; all incorporated herein by reference in their entirety, describe this work in more detail.

In copending U.S. provisional application 61/515,500, also incorporated herein by reference in its entirety, techniques for forming crystalline everolimus or another macrolide drug from slurries of amorphous drug have been described. The crystalline form has a lower water solubility and that lower solubility has several advantages, including permitting a lower drug coat weight needed to provide an therapeutic dose at the device location over an extended period and allowing for manipulation of the release rate independent of a polymer. Achieving these advantages in practice, however, depends on an ability to provide a reliably adherent coat of drug without any polymer present. The present invention pertains to devices and methods in which a crystalline form drug coating is formed on a device from an amorphous drug coating layer by seeding a surface of the device, before or after application of the amorphous drug layer, and then vapor annealing the coating with a solvent vapor.

Everolimus is supplied by the vendor as an amorphous solid. Coating a device with an everolimus coating solution leads to a coating in which the everolimus is in the amorphous state. Given the fact that the aqueous solubility of amorphous everolimus is greater than amorphous paclitaxel, and amorphous paclitaxel dissolves too rapidly to provide sustained drug tissue levels when delivered without a polymer to modulate release, it is likely that it will not be possible to attain adequate drug tissue duration with a drug eluting balloon (DEB) based on amorphous everolimus without use of a polymer. Formulations with polymers, however, are undesirable because placing a polymer at the treatment site introduces a complicated set of tissue compatibility and degradation issues which may be different for each drug or drug form used and for delivery at different tissue sites.

Figure 1:
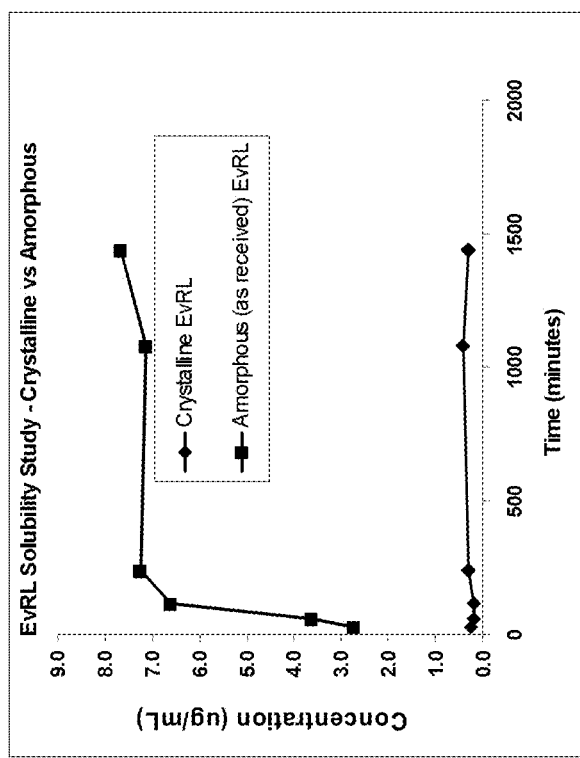
FIG. 1 is a graph comparing everolimus solubility data in water @ 37° C. for amorphous and crystalline forms.

Studies by the owner of this application have shown that crystalline everolimus has a much lower solubility in water than amorphous everolimus. Everolimus solubility data (in water @ 37° C.) is shown in FIG. 1. A medical device such as a stent or balloon having a polymer-free coating based on a crystalline drug such as everolimus is useful for obtaining a dissolution-controlled drug release coating that does not rely on polymer.

Figure 2:
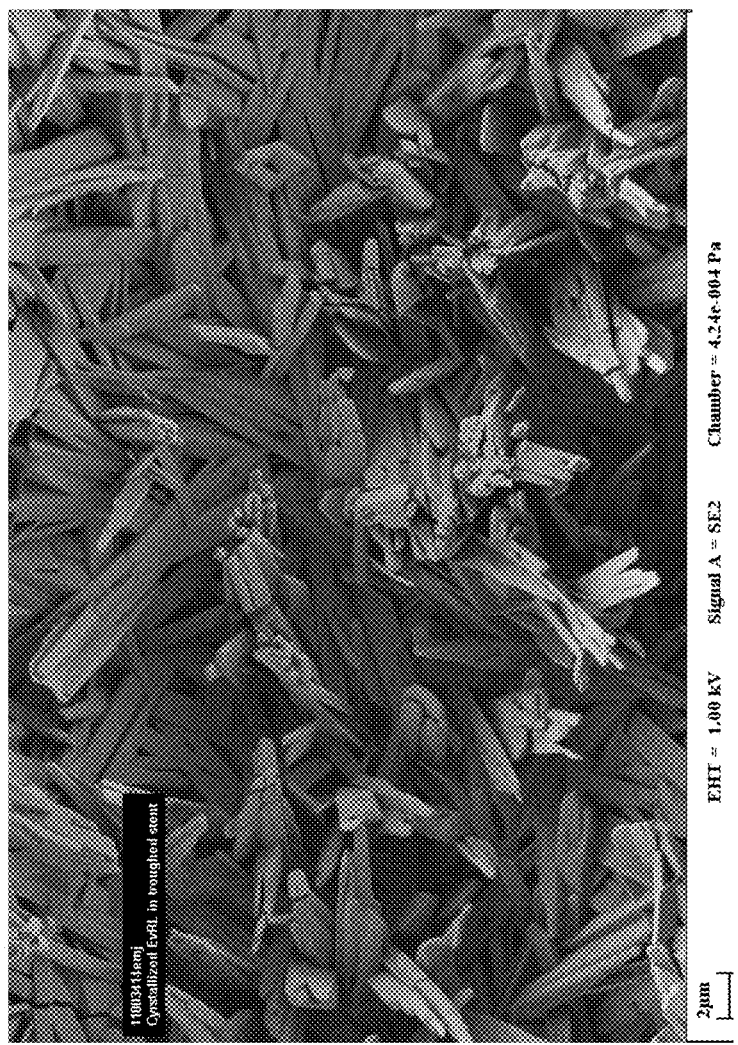
FIG. 2 is an enlarged SEM of the crystalline structure of a stent coating of the invention.

FIG. 2 is an SEM of an everolimus drug coating on a stent prepared in accordance with the invention. The figure shows tightly packed rectilinear crystals having an estimated length of about 5-15 μm, width of about 0.5-1.5 μm and thickness of about 0.3 μm, based on the scale provided at the lower left of the figure.

Drugs

According to some embodiments of the invention the drug is one that has crystalline and amorphous forms, and is desirably delivered in a crystal form. The drugs which can be used in embodiments of the present invention, can be any therapeutic agent or substance that has therapeutic benefit for local administration by delivery from a medical device inserted into the body and that also exists in such polymorph forms. In this aspect the drug is coated on the device, with or without an excipient, in an amorphous form and then is converted to the desired crystalline form in an annealing step that grows the crystalline drug in the coating in-situ on the device. This gives a packed system of crystals on the surface that more closely approximate the desired properties of a drug delivery balloon.

In some embodiments the drug is a lipophilic substantially water insoluble drug that inhibits restenosis, for instance rapamycin, rapamycin analogous and derivatives, everolimus, everolimus analogous and derivatives, paclitaxel analogous and derivatives, and mixtures thereof. The drug is suitably one that is able to form a crystalline form by treatment with a solvent or solvent vapor after it is applied to the device.

In some embodiments, the drug may be a macrolide immunosuppressive (limus) drug. In some embodiments, the macrolide immunosuppressive drug is rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 40-O-(6-Hydroxy)hexyl-rapamycin 40-O-[2-(2-Hydroxy)ethoxy]ethyl-rapamycin 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42 S)-42-Deoxy-42-(1H-tetrazol-1-yl)-rapamycin (zotarolimus), or derivative, isomer, racemate, diastereoisomer, prodrug, hydrate, ester, or analog thereof, provided that the particular drug is one has an amorphous form and a crystalline form.

In some embodiments, the drug may be everolimus, sirolimus, zotarolimus and/or biolimus. In some embodiments the drug is everolimus.

Other drugs for which the inventive conversion method that may be useful include antiinflammatory agents such as dexamethasone, prednisolone, corticosterone, budesonide, estrogen, sulfasalazine, mesalamine, and analogues thereof; antineoplastic/antiproliferative/anti-miotic agents such as paclitaxel, 5-fluorouracil, cisplatin, vinblastine, vincristine, epothilones, endostatin, angiostatin, thymidine kinase inhibitors, and analogues thereof; anesthetic agents such as lidocaine, bupivacaine, ropivacaine, and analogues thereof; anti-coagulants; and growth factors, again provided that the particular drug is one has an amorphous form and a crystalline form.

Excipients

In some embodiments the drug is formulated with a non-polymeric excipient. An excipient is an non-polymeric additive to a drug-containing layer that facilitates adhesion to the device and/or alters release properties from the device upon placement at a treatment site. In at least some embodiments using an excipient the drug is substantially insoluble in the excipient. In at least some embodiments using an excipient, the excipient and amorphous drug are dissolved in a common solvent which is then applied to the device to form the an amorphous drug layer that further comprises the expedient. An excipient may also be applied by concurrent spraying of separate solvent solutions of the drug and the excipient.

Typically the non-polymeric excipient will provide less complications because it has a much shorter residence time at a treatment site. This however means that it may not have much influence on an extended residence time for the drug at the site.

Examples of excipients that may be employed include polymeric and non-polymeric additive compounds, including sugars such as mannitol, contrast agents such as iopromide, citrate esters such as acetyl tributyl citrate, acetyl triethyl citrate, tributyl citrate, triethyl citrate, acetyltri-n-hexyl citrate, n-butyryltri-n-hexyl citrate, acetyltri-n-(hexyl/octyl/decyl) citrate, and acetyltri-n-(octyl/decyl) citrate; glycerol esters of short chain (i.e. $C_2$-$C_8$) mono-carboxylic acids such as triacetin; and pharmaceutically acceptable salts.

Exemplary non-polymeric excipients include citrate esters, such as acetyl tributyl citrate or other acetylated trialkyl citrates, trialkyl citrates, and trialkyl citrates that have been etherified at the hydroxyl group on citric acid. Other non-polymeric excipients that may be useful include surfactants such as described in US 2008/0118544 A1; oils; esters of fatty acids and $C_1$-$C_{30}$ alcohols such as isopropyl myristate; triacetin; and the like. Other documents in which describe non-polymeric excipients that may be useful include US 2005/0101522 A1; US 2006/0020243 A1; US 2008/0255509 A1; US 2010/0063585 A1; US 2010/0179475 A1; and US 2010/0272773 A1. In at least some embodiments the excipient is selected to be one in which the drug is substantially undissolved, so that the major portion of the drug remains in the crystalline form.

In at least some embodiments no excipient is used.

Devices

The medical devices used in conjunction with the present invention include any device amenable to the coating processes described herein. The medical device, or portion of the medical device, to be coated or surface modified may be made of metal, polymers, ceramics, composites or combinations thereof. Whereas the present invention is described herein with specific reference to a vascular stent or balloon, other medical devices within the scope of the present invention include any devices which are used, at least in part, to penetrate the body of a patient. Non-limiting examples of medical devices according to the present invention include catheters, guide wires, balloons, filters (e.g., vena cava filters), stents, stent grafts, vascular grafts, intraluminal paving systems, soft tissue and hard tissue implants, such as orthopedic repair plates and rods, joint implants, tooth and jaw implants, metallic alloy ligatures, vascular access ports, artificial heart housings, artificial heart valves, aneurysm filling coils and other coiled coil devices, trans myocardial revascularization ("TMR") devices, percutaneous myocardial revascularization ("PMR") devices, hypodermic needles, soft tissue clips, holding devices, and other types of medically useful needles and closures, and other devices used in connection with drug-loaded polymer coatings.

Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like. Any exposed surface of these medical devices which may enter the body may be coated with the coating and methods of the present invention.

In some embodiments the drug is provided on stents or other devices implanted or left in place for extended times in the body. In some embodiments the drugs are deliverable from the surface of catheter balloons which is transiently provided at a site of treatment, expanded to release the drug and then removed. The devices of the present invention, may be deployed in vascular passageways, including veins and arteries, for instance coronary arteries, renal arteries, peripheral arteries including illiac arteries, arteries of the neck and cerebral arteries, and may also be advantageously employed in other body structures, including but not limited to arteries, veins, biliary ducts, urethras, fallopian tubes, bronchial tubes, the trachea, the esophagus and the prostate.

In some embodiments the invention pertains to a stent coated with polymer-free coating comprising crystalline everolimus.

Seeding

Some embodiments involve applying an amorphous drug coating to a device that has been first nucleated with microparticulate crystalline drug to induce crystallization during the annealing step. In some embodiments a coating of amorphous drug is applied to the device and then nucleated by applying microparticulate crystalline drug to the amorphous drug layer, followed by vapor annealing. These two may also be combined so that microcrystalline drug is applied under and over the amorphous drug layer before vapor annealing.

The microcrystalline drug may be applied dry, using powder application equipment, for instance charged particle applicators or from suspension. The device may be dipped and withdrawn from an agitated suspension, or applied using e.g. a spray or syringe to apply a dispersion of the microparticulate drug, followed by drying. For a drug such as everolimus a suitable suspension vehicle for dispersing the microcrystalline drug is water. Suitable methods for preparing the microparticulate crystalline drug include crystallizing the drug from solution or slurry and then grinding the drug crystals to the desired size range.

In some embodiments the microparticulate nucleating agent is provided on the substrate, before application of the drug coating at a density of from about 10 particle/mm² to about 5000 particles/mm², or from about 100 particles/mm² to about 2000 particles/mm². The size of the microparticulate drug nucleating agent may vary. In some embodiments the particulate nucleating agent has its major dimension in the size range of from about 10 nm to about 20 µm, or from about 100 nm to about 10 µm.

Alternatively the amorphous coating may be generated first. Then a microcrystalline layer applied, followed by solvent vapor annealing.

In at least some embodiments the microparticulate drug crystals in such a coating have a mean particle size of less than about 10 µm as measured by dynamic light scattering methods, for instance using photocorrelation spectroscopy, laser diffraction, low angle laser light scattering (LALLS), medium-angle laser light scattering (MALLS), light obscuration methods (Coulter method, for example), rheology, or microscopy (light or electron). The microparticles can be prepared in a wide range of sizes, such as from about 20 µm to about 10 nm, from about 10 µm to about 10 nm, from about 2 µm to about 10 nm, from about 1 µm to about 10 nm, from about 400 nm to about 50 nm, from about 200 nm to about 50 nm or any range or combination of ranges therein. The crystalline particle size in some cases may be sized to a desired distribution using agitation methods such as sonication during slurry aging. Alternatively a desired particle size may be obtained by mechanical grinding techniques such as pearl milling, a ball milling, hammer milling, fluid energy milling or wet grinding techniques or the like after the drug has been converted to crystalline form.

In an exemplary method of preparing microparticulate everolimus, a slurry of the everolimus crystals in a non-solvent such as water or heptane is prepared in stainless steel ampule. Milling media (for instance micro-beads of a hard durable material such as zirconia) is added to the slurry. The ampule is placed on a high speed shaker and shaken at 4000 rpm for 20 min. The shaking process results in cascading of the media in the ampule which acts to break the everolimus crystal into small micro or nano-sized particles.

Alternatively a slurry of the everolimus crystals in a non-solvent such as water or heptane may be prepared in a glass vial or bottle. Milling media (for instance micro-beads of a hard durable material such as zirconia) is added to the slurry. The vial or bottle may be placed on a roller mill for about 24 hr. The rolling process results in cascading of the media in the vessel which acts to break the everolimus crystals into small micro- or nano-sized particles.

Particle size is dictated by the diameter and composition of the milling media. Spherical media is available in various diameters and composition (densities). Reducing the diameter of the media usually results in smaller drug particles. Increasing the density of the media results in greater milling energy and smaller drug particles. It is desirable to break the drug particles down to a size where a reasonably stable coating dispersion can be obtained that can then be coated by various coating processes such as electrostatic spraying, powder spray, spin coaters. Exemplary coater systems include e.g., LabCoat®, or Direct Write® (from Optimec) coating systems).

It is surprising that microcrystalline drug can be used as a nucleating agent under the amorphous drug coating applied from solution. Generally it was expected that the microcrystalline drug would dissolve if a drug solution was applied to it unless the microcrystalline layer was so thick that it formed a weak boundary. Either way it was considered that that nucleation with microcrystalline drug particles should not provide a reliable crystalline coating for a medical device.

Amorphous Drug Layer

The amorphous drug layer is suitably applied from solution, although other techniques may also be used. Solution coating provides good surface coverage and coating quality. When microcrystalline drug has been applied before the amorphous drug layer, the solution application technique should be carried out in a way that provides rapid drying, so that at least some of the microcrystalline drug survives to nucleate crystallization in the vapor annealing step. The solution concentration, temperature, application technique and the pressure in an tank or vessel where the solution is applied can be manipulated to provide a suitable drying rate. In some embodiments the amorphous drug layer is applied by spraying, dipping, roll coating, or the like.

In some embodiments the amorphous drug layer is applied by spraying, using equipment that allows for variation in nozzle pressure, distance from substrate, and gas mixing ratios to provide a coating that largely dries on route to the substrate so that the applied coating is essentially dry on impact. In some cases the amorphous drug layer is applied so that enough of the solvent remains on impact to provide a smooth coating of the amorphous drug.

Vapor Annealing

The vapor annealing step is performed using a solvent that is effective to induce crystallization for the drug employed. The use of the microcrystalline drug as nucleating agent has the advantage that it does not introduce another component to the device coating that needs to be accounted for in evaluating the safety and efficacy of the coated device.

Examples of solvents that may be used include alcohols such as methanol, ethanol (EtOH), isopropanol (IPA), n-butanol, isobutyl alcohol or t-butyl alcohol; acetonitrile (ACN); ethers such as tetrahydrofuran (THF) isopropyl ether (IPE), diethyl ether (DEE); ketone solvents such as acetone, 2-butanone (MEK), or methyl isobutyl ketone (MIBK); halogenated solvents such as dichloromethane (DCM), monofluorobenzene (MFB), α,α,α-trifluorotoluene (TFT), nitromethane (NM), ethyl trifluoracetate (ETFA); aliphatic hydrocarbons such as hexane, heptane, or the like; aromatic hydrocarbons, such as toluene or xylenes; and ester solvents such as ethyl acetate. Mixed solvents, for instance heptane/ethyl acetate, acetone/water, IPA/water, or IPA/THF, THF/heptane can also be used.

In some cases a non-volatile solute may be mixed with the vapor annealing solvent to limit vapor pressure of the solvent in the treatment chamber. If the solvent vapor pressure (partial pressure) is too low no crystallization occurs. If too high there is a potential for the coating to become too fluid and the coating can migrate on the stent. Generating the solvent vapor from a solution of a non-volatile solute in the solvent allows adjustment of the solvent vapor pressure to be optimized for a particular coating.

Vapor annealing time for forming the crystalline drug on the balloon may range widely, for instance from about 5 minutes to about 24 hours, or even longer. A typical time may be at least 30 minutes up to about 16 hours. The solvent suitably is one that induces crystallization of the drug without attacking the substrate material of the device. In some embodiments an alcohol solvent is employed, for instance a $C_1$-$C_4$ alcohol.

After the vapor annealing step the balloon catheter may be dried in a vacuum oven or by exposure to ambient conditions. In some embodiments a vacuum drying step may also contribute to improvement of coating durability as compared to ambient drying conditions.

An exemplary method of preparing a vapor annealed coating of Everolimus is as follows. An Element® (Boston Scientific Corporation) stent is first abluminally coated with microparticulate everolimus and dried. The microparticulate coating may be at or below gravimetric detection limits (about 2 µg or less). In a second coating step a solution of Everolimus is then abluminally coated via either electrospray, Direct Write™, or by Anilox roll coat in a therapeutic amount. The Everolimus as coated in the second step is amorphous. The stent is vapor annealed by exposing the stent to isopropyl alcohol vapor overnight to generate the crystalline morphology. The drug can be coated with or without an excipient. Examples of appropriate excipients are fatty acid and fatty acid derivatives.

The importance of seeding to production of a useful coating is illustrated in FIGS. 8a and 8b, provided for comparison. In FIG. 8a an amorphous everolimus coating is shown, without seeding. FIG. 8b shows the same coating after treatment with IPA vapor. As can be seen the drug has migrated off of major areas of the stent and concentrated at particular points where very large needle-like crystals gave grown. The crystals have poor adherence to the stent and their large size makes it easy to dislodge them.

Mixed Form Coatings

In addition to creating coatings of a specific drug crystalline form it is desirable to prepare a device coating that possesses a blend of amorphous and crystalline forms within the same coating. The faster dissolving amorphous drug will provide for initial burst release to the vessel and crystalline phase(s) will provide for slower dissolution into the vessel for sustained tissue levels. This can be accomplished for example by first applying a minor layer of microcrystalline drug, suitably from suspension in a non-solvent. Next, generate an amorphous coating. Finally subjecting the amorphous coating to solvent vapor annealing (e.g. isopropanol vapor) for time intervals less than required to achieve 100% crystallinity will lead to a coating with a mix of amorphous and crystalline phases. A specific rate of drug release from the coating may be tailored by varying the ratio of these drug polymorphs with different solubility and dissolution rates in a single coating.

In some embodiments the fraction of amorphous drug in the coating is from 0-25%, for instance about 1%, about 2%, about 3%, about 5%, about 6%, about 8%, about 10%, about 12%, about 15%, about 18%, about 20%, about 22%, or about 25%, based on total drug weight. In some embodiments the fraction of crystalline drug is from 1% to 100%, for instance 1-99%, 5-95%, about 10%, about 15%, about 20%, about 25%, about 30%, about 35%, about 40%, about 45%, about 50%, about 55%, about 60%, about 65%, about 70%, about 75%, about 80%, about 85%, about 88%, about 89%, about 90%, about 91%, about 92%, about 93%, about 94%, about 95%, about 96%, about 97%, about 98%, about 99% or about 100%, based on total drug weight.

Coat Weight

In some embodiments a drug coating of drug on a device such as a sent or drug delivery balloon contains from 10 to 1000 µg of drug, for instance 10-200 µg, 200-800 µg, 300-600 µg, or 400-500 µg of everolimus. In some embodiments the amount of amorphous drug on the device is from 0-80 µg, less than 60 µg, or less than 30 µg, with the remaining being a crystalline form.

In some embodiments the amount of amorphous drug on the device is from 0-80 µg, less than 60 µg, or less than 30 µg, with the remaining being one or both crystalline forms. In some embodiments the amount of crystalline drug on the device is from 10 to 1000 µg, 10-200 µg, 100-800 µg, 200-600 µg, 300-500 or 350-450 µg.

In some embodiments the fraction of amorphous drug in the coating is from 0-25%, for instance about 1%, about 2%, about 3%, about 5%, about 6%, about 8%, about 10%, about 12%, about 15%, about 18%, about 20%, about 22%, or about 25%, based on total drug weight. In some embodiments the fraction of crystalline drug is from 1% to 100%, for instance 1-99%, 5-95%, about 10%, about 15%, about 20%, about 25%, about 30%, about 35%, about 40%, about 45%, about 50%, about 55%, about 60%, about 65%, about 70%, about 75%, about 80%, about 85%, about 88%, about 89%, about 90%, about 91%, about 92%, about 93%, about 94%, about 95%, about 96%, about 97%, about 98%, or about 99%, based on total drug weight.

The invention is illustrated by the following non-limiting examples.

Example 1

Generation of Crystalline Everolimus Via Seeding and Vapor Annealing a. Preparation of Microcrystalline Everolimus Amorphous everolimus is dissolved in isopropyl alcohol at 40 wt % with gentle warming at ~40 C. The solution is allowed to sit at RT overnight resulting in crystallization of the everolimus. The large crystals are dried under vacuum at RT. 0.1 g of crystalline everolimus, 0.16 g water and 1.85 g of 100 um Zirconia beads are added to a SS ampule. The ampule is sealed and placed on a high speed amalgamator shaker for 20 min. Water (2 mL) is added to the resulting paste and the mixture is swirled to disperse the milled everolimus particles.

The water/everolimus dispersion is decanted off from the Zr beads and filtered through a 30 um nylon mesh filter. The Zr bead slurry is washed an additional 3 times using about 2 mL water each time and each time the water/everolimus dispersion is filtered through 30 µm nylon mesh filter. The combined filtered dispersion is centrifuged at 4000 rpm for 10 min. The supernatant is decanted off until there is about 1-2 mL of liquid remaining in the centrifuge tube along with the everolimus particles. The concentrated particle dispersion is transferred to a vial. The centrifuge tube is then rinsed 2-3 times with 0.1-0.2 mL DI water (each rinse) and added to the vial (to transfer residual dispersion clinging to the walls of the centrifuge tube). The resulting everolimus dispersion in water is about 3 wt % solids. Yield is about 70%. Average particle size is about 1 µm.

b. Seeding, Coating and Vapor Annealing of Everolimus Coated Stents

Figure 3:
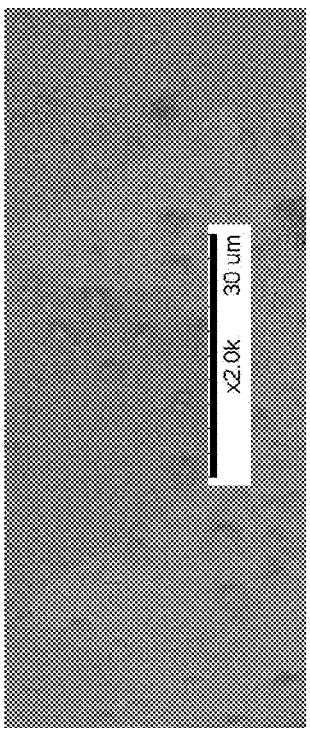
FIG. 3 shows a representative SEM of the seeded stent showing traces of microcrystalline everolimus.

The aqueous microcrystalline everolimus dispersion resulting from Example 1a is sprayed onto 16 mm stents using an electrospray process. Flow rate is 0.5 mL/hr. Spray time is 20-30 sec. A very small amount of the everolimus particles are coated on the stent. The coat weight was too little to quantify gravimetrically (a rough estimate is 1-3 µg. FIG. 3 shows a representative SEM of the seeded stent showing traces of microcrystalline everolimus.

The seeded stent is then coated via electrospray with everolimus (3% everolimus in 1:1 THF:IPA. Flow rate is 2-3 mL/hr). The coat wt of the amorphous drug layer is 100-200 µg.

Figure 4:
FIG. 4 shows a representative SEM of a stent coated with amorphous everolimus using a nominal spray process which provides a smooth coating.

FIG. 4 shows a representative SEM of a stent coated with amorphous everolimus using a nominal spray process which provides a smooth coating.

Figure 5B:
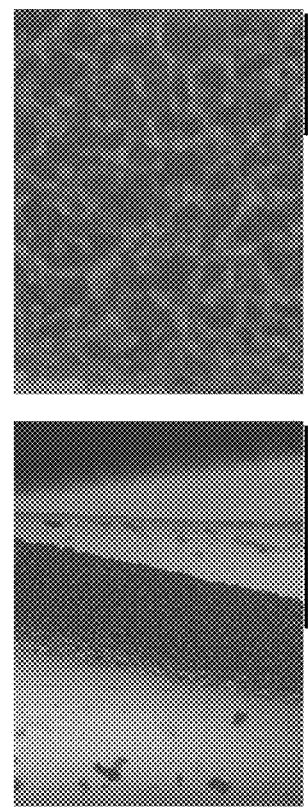
FIGS. 5a and 5b show a representative SEM of a stent coated with amorphous everolimus using a dry spray process, at two different magnifications.
Figure 5A:
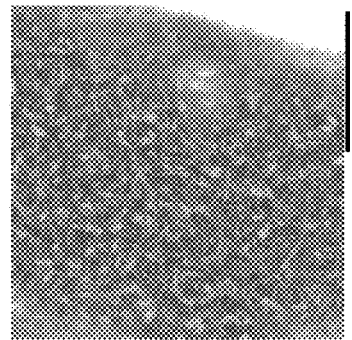

FIGS. 5a and 5b show a representative SEM of a stent coated with amorphous everolimus using a dry spray process, at two different magnifications. The dry spray is produced by the same apparatus by increasing the distance, reducing the flow rate but increasing the spray time, to give an equivalent weight coating. The dry spray process results in a more porous (matte-like) coating but remains amorphous.

The vapor annealing process is conducted as follows: About 2 mL of 70/30 (wt/wt) of IPA/glycerol is added to the bottom of the 8 oz jar. The stents are suspended above the liquid. The jar is sealed at RT for ~24 hr. The glycerol is a non-volatile solute used to control the vapor pressure of the IPA in the jar. It has been found that the resulting crystalline morphology is impacted by the IPA vapor concentration in the jar. A 75/25 ratio of IPA/glycerol was found to give optimal crystal morphology.

Figure 6:
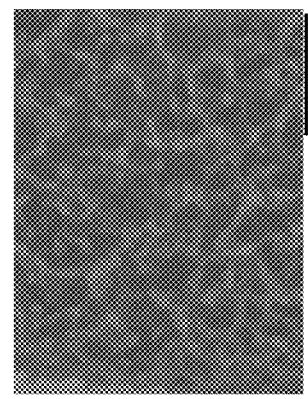
FIG. 6 shows a representative SEM of a vapor annealed seeded stent (using the nominal everolimus coating).

FIG. 6 shows a representative SEM of a vapor annealed seeded stent (using the nominal everolimus coating).

FIGS. 7a and 7b show representative SEM of a vapor annealed seed stent (using the dry everolimus coating process), at two different magnifications. A very small, uniform crystalline structure is formed during vapor annealing.

Differential scanning calorimetry (DSC) of vapor annealed everolimus shows a crystalline melting endotherm at 154 C. There is no visible glass transition (Tg) at about 80 C (the Tg of amorphous everolimus is about 80 C). Thus DSC shows that vapor annealed everolimus is crystalline.

Comparative Example

Vapor Anneal Without Seeding

As a comparative example of omitting the microparticulate crystalline drug, method a solution of Everolimus is abluminally coated onto an Element® (Boston Scientific Corporation) stent via electrospray similar to Example 1. The everolimus as coated is amorphous (FIG. 8a). The stent is vapor annealed by exposing the stent to isopropyl alcohol vapor overnight (FIG. 8b) to generate the crystalline morphology.

As can be seen, the drug has migrated. The crystals are very long needles poorly adhered to the stent.

Example 2

Porcine Animal Study of Everolimus Coated Stents

Stents coated with either crystalline or amorphous everolimus (130 μg on 12 mm stents) were implanted in the coronary arteries and internal thoracic arteries of common swine. The stented vessels were explanted after 3 hrs, 24 hrs, 7, 14 and 28 days. N=3 stents per timepoint were used. After sacrifice the stents were removed from the arteries and the amount of drug in the arteries was determined by LC/MS. The amount of drug remaining on the stent was determined by HPLC. Table 1 shows the amount of drug remaining in the tissue after 28 days and the amount of drug remaining on the stents. There is essentially no drug in the tissue at 28 days for stents coated with amorphous everolimus compared to 6 ng/mg for crystalline everolimus. There was no drug remaining on the stents after 28 days for the amorphous drug compared to 25% drug remaining on the stent with crystalline everolimus. This example shows the significant benefit of using the slower dissolving/lower solubility crystalline form of the drug in maintaining significant drug tissue levels.

TABLE 1

| Stent coating | Tissue content at 28 days | % drug left on stent at 28 days |
| --- | --- | --- |
| Amorphous Everolimus | 0.04 ng/mg | 0 |
| Crystalline Everolimus | 6.1 ng/mg | 25.8 |

Example 3

Crystalline Everolimus Coated Balloon Via Seeded Vapor Annealing

A 3 mm×16 mm balloon was syringe coated with 2 μL of a 1.4% solids everolimus microdispersion to provide the seeding layer. The coating was allowed to dry at RT. The balloon was then coated with 11 μL of a 3.8% soln. of everolimus in 75/25 (wt/wt) acetone/water to give a coat wt of about 3 ug/mm2 The balloon was vapor annealed with IPA vapor overnight to crystallize the everolimus. FIG. 10 shows a SEM image of the balloon showing the presence of crystalline everolimus.

Example 4

Coating of Balloon with Microcrystalline Everolimus

Figure 9:
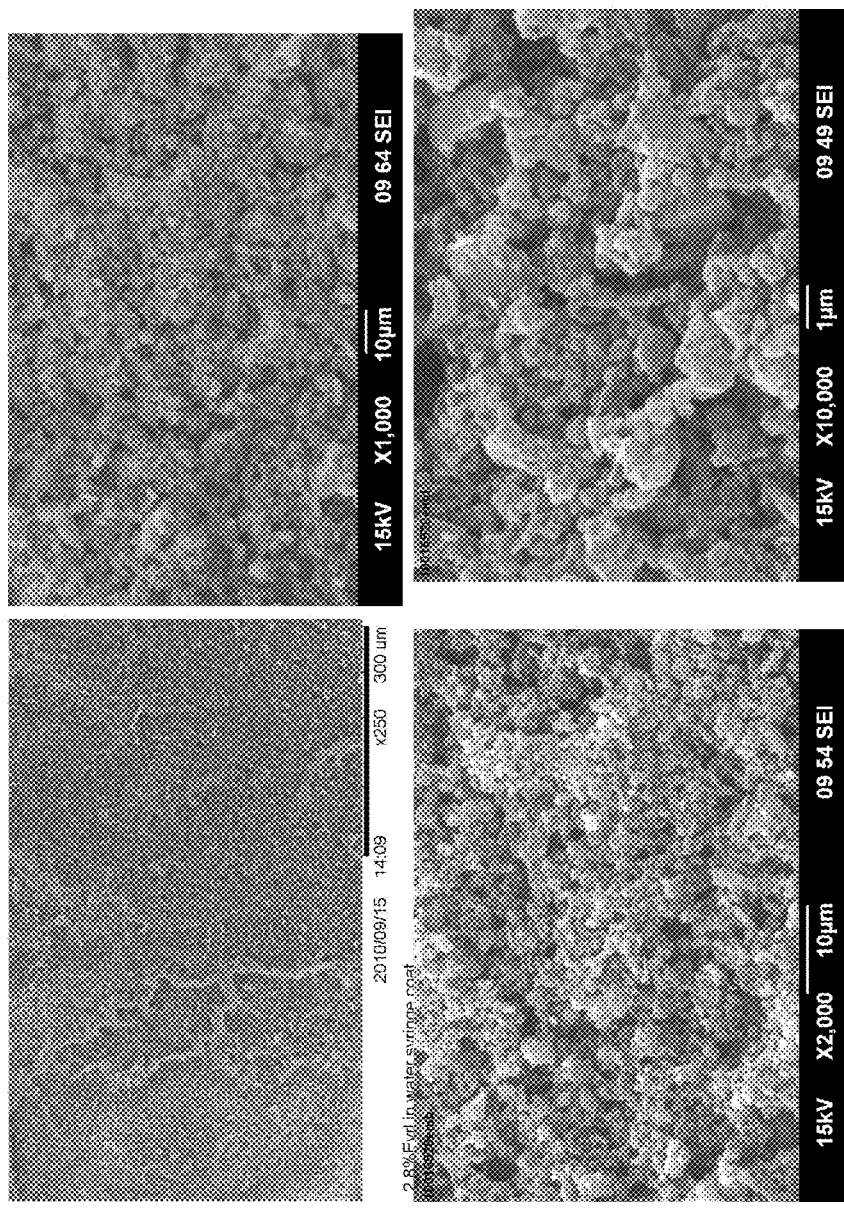
FIG. 9 shows SEM images of a coated balloon as described in Example 4, at 4 magnifications.

A 3 mm×16 mm balloon was syringe coated with 15 μL of ~3% everolimus microdispersion in water. The coating was dried at RT. The resulting drug content was 3 μg/mm². FIG. 9 shows SEM images of the coated balloon showing the morphology of the microparticles of everolimus at 4 magnifications.

Other coating processes can be utilized which would allow one to abluminally coat crystalline drug or both amorphous and crystalline drug. For example, Direct Write® (Optimec) allows one to abluminally coat discrete dots of drug. FIG. 11 shows an example of a coating of discrete dots of a drug on a substrate. Using this coating process one can first partially coat the stent with discrete dots of everolimus. The stent can then be vapor annealed to generate crystalline drug dots. This is illustrated in FIG. 12, wherein a portion 12 of a stent 10 is shown having dots of crystalline drug 14 thereon.

The stent 20 illustrated in FIG. 13, is prepared in a manner similar to the stent 10 of FIG. 12, but after forming crystalline drug dots 14 same stent can again be coated with discrete dots 18 of amorphous drug. The stent is not subsequently vapor annealed—leaving the second coating amorphous. In this way modulate release by having amorphous everolimus to give predominately burst release and crystalline everolimus to provide predominately sustained release. The balance of burst to sustained release can by adjusted independently through control of the proportional coat weights of the amorphous and crystalline dots.

In still another embodiment, not shown, the microparticulate crystalline drug and the amorphous drug are coated onto a stent with troughs or depressions on the surface, either applying the drug directly into the troughs or depressions only, or onto the stent followed by removal, e.g. by wiping, from the portions of the stent outside the troughs. Vapor annealing produces a drug coating in accordance with the invention that is confined to the troughs or depressions. This provides some additional protection for the crystalline drug coating during delivery while still allowing the benefit of a polymer-free drug that provides extended release.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively in each singly dependent claim format which creates a dependency from an antecedent-possessing claim other than the specific claim listed in such dependent claim.

The invention claimed is:

1. A method of forming a coating comprising a drug on at least a portion of an outer surface of a medical device, the drug being a member of the group consisting of everolimus, tacrolimus, sirolimus, zotarolimus, biolimus, and rapamycin, the method comprising the steps of:
  providing a medical device;
  applying a solution of the drug to said portion of the outer surface to form a coating of amorphous drug;
  providing crystals of the drug;
  grinding the crystals of the drug to form microcrystals of the drug having a maximum size of about 10 μm or less;
  applying the microcrystals of the drug to at least said portion of the outer surface of the device; and vapor annealing the coating of amorphous drug with a solvent vapor to form crystalline drug; the solvent selected from the group consisting of alcohols, acetonitrile, ethers, ketones solvents, halogenated solvents, aliphatic hydrocarbons, aromatic hydrocarbons, and ester solvents, wherein the microcrystals of the drug are applied before or after applying the drug solution, but prior to any vapor annealing of the coating of amorphous coating.

2. A method as in claim 1 wherein the drug is everolimus.

3. A method as in claim 1 wherein the microcrystals of the drug form a seed layer on the portion of the outer surface of the device having a coat weight of less than 0.05 µg/mm².

4. A method as in claim 1 wherein the microcrystals are seed layer is applied from suspension in a liquid vehicle.

5. A method as in claim 1 wherein the solvent vapor is generated by vaporization of a liquid solvent composition in a chamber and the liquid solvent composition further comprises a non-volatile solute.

6. A method as in claim 1 wherein the medical device is a stent.

7. A method as in claim 6 wherein the device is a metal stent having grooves or depressions thereon, the drug solution is free of any excipient, and the drug solution is applied to said grooves or depressions on the outer surface of the stent.

8. A method of forming a coating comprising a drug on at least a portion of an outer surface of a medical device, the drug being a member of the group consisting of everolimus, tacrolimus, sirolimus, zotarolimus, biolimus, and rapamycin, the method comprising the steps of:

applying a solution of the drug to said portion of the outer surface to form a coating of amorphous drug;

providing crystals of the drug;

preparing a microcrystalline form of said drug by breaking the crystals of the drug into microcrystals having a maximum particle size of about 10 µm or less;

applying the microcrystals to at least said portion of the outer surface of the device; and subsequently vapor annealing the amorphous coating with a solvent vapor to form crystalline drug; the solvent vapor consisting of a vapor of a solvent selected from the group consisting of alcohols, acetonitrile (ACN); ethers, ketones solvents, halogenated solvents, aliphatic hydrocarbons, aromatic hydrocarbons, and ester solvents, wherein the microcrystals are applied to at least said portion of the outer surface of the device before or after applying the drug-solution, but prior to any vapor annealing of the amorphous coating.

9. A method as in claim 8 wherein the medical device is a catheter balloon.

10. A method as in claim 9 wherein the drug is everolimus.

11. A method as in claim 8 wherein the medical device is a stent.

12. A method as in claim 11 wherein the drug is everolimus.

13. The method of claim 6 wherein the medical device is a catheter balloon.

14. The method of claim 8 wherein the step of preparing a microcrystalline form of said drug comprises the step of grinding the crystallized drug to a desired size range.

15. The method of claim 8 wherein during the step of preparing a microcrystalline form of said drug, the drug crystals are subjected to sonication in a slurry.

16. A method of forming a coating comprising a drug on at least a portion of an outer surface of a medical device, the drug being a member of the group consisting of everolimus, tacrolimus, sirolimus, zotarolimus, biolimus, and rapamycin, the method comprising the steps of:

providing a medical device;

applying a solution of the drug to said portion of the outer surface to form a coating of amorphous drug;

providing seed crystals of the drug, the seed crystals having a major dimension ranging from about 10 nm to about 20 µm;

disposing the seed crystals of the drug on at least said portion of the outer surface of the device;

vapor annealing the drug with a solvent vapor to form crystalline drug; the solvent selected from the group consisting of alcohols, acetonitrile, ethers, ketones solvents, halogenated solvents, aliphatic hydrocarbons, aromatic hydrocarbons, and ester solvents, wherein the seed crystals of the drug are applied to at least said portion of the outer surface of the device before or after applying the drug solution, but prior to subjecting the medical device to any vapor annealing.

* * * * *